United States Patent
Kozlowski et al.

[11] Patent Number: 6,066,636
[45] Date of Patent: May 23, 2000

[54] MUSCARINIC ANTAGONISTS

[75] Inventors: Joseph A. Kozlowski, Princeton; Stuart W. McCombie, Caldwell; Jayaram R. Tagat, Westfield; Susan F. Vice, Mountainside, all of N.J.

[73] Assignee: Schering Corporation, Kenilworth, N.J.

[21] Appl. No.: 09/340,466

[22] Filed: Jun. 28, 1999

Related U.S. Application Data

[60] Provisional application No. 60/091,218, Jun. 30, 1998.

[51] Int. Cl.[7] .................. A61K 31/496; C07D 405/14; C07D 401/14; C07D 403/14; C07D 409/14
[52] U.S. Cl. .................. 514/252; 544/238; 544/360; 544/364; 544/379; 546/187; 546/193; 546/194; 546/212; 546/213; 514/316; 514/318; 514/326
[58] Field of Search .................. 544/238, 360, 544/364, 379; 514/252

[56] References Cited

U.S. PATENT DOCUMENTS

| | | | |
|---|---|---|---|
| 4,895,841 | 1/1990 | Sugimoto et al. | 514/212 |
| 5,061,704 | 10/1991 | Wierzbicki et al. | 544/379 |
| 5,889,006 | 3/1999 | Lowe et al. | 519/252 |

FOREIGN PATENT DOCUMENTS

| | | |
|---|---|---|
| 0 229 391 | 7/1987 | European Pat. Off. |
| 0 346 791 | 12/1989 | European Pat. Off. |
| WO 93/00906 | 1/1993 | WIPO |
| WO 96/26196 | 8/1996 | WIPO |

OTHER PUBLICATIONS

Baumgold, et al., European Journal of Pharmacology 251 (1994) 315–317.
Melchiorre, et al., J. Med. Chem, 1993, 36, 3734–3737.
Logemann, et al., Brit. J. Pharmacol (1961) 17, 286–296.
Watson et al, *J. Pharmacol. Exp. Ther.,* 237 (1986), p. 411–418.
Cheng et al, *Biochem. Pharmacol.,* 22 (1973), p. 3099–3108.
Eberlein, et al., Trends in Pharmacol Sci Dec. 1989 p 50–54.
Doods, et al., Life Sciences, vol. 52, pp. 497–503 (1993).
Kamiya et al, *Chem. Pharm. Bull.,* 21 (7) 1510–15 (1973).
Carcellar et al., *Chemical Abstracts,* vol. 125, No. 275911 (1996).
Kuno et al, *Chem. Pharm. Bull.* 41 p. 156–162 (1993).
Ward et al, *J. Med. Chem.* 35, p. 4011–4019 (1992).
Quirion et al., *Tips,* p 80–84 (1989).

*Primary Examiner*—Emily Bernhardt
*Attorney, Agent, or Firm*—Anita W. Magatti

[57] ABSTRACT

Heterocyclic derivatives of di-N-substituted piperazine or 1,4 di-substituted piperidine compounds in accordance with formula I (including all isomers, salts and solvates)

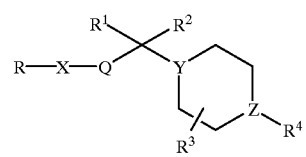

wherein
wherein one of Y and Z is —N— and the other is —N— or —CH—;
X is —O—, —S—, —SO—, —SO$_2$— or —CH$_2$—;
Q is

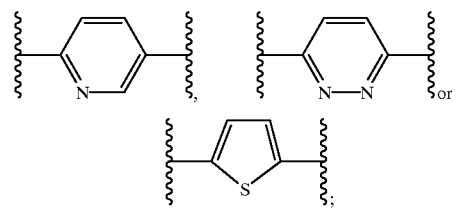

R is alkyl, cycloalkyl, optionally substituted aryl or heteroaryl;
R$^1$, R$^2$ and R$^3$ are H or alkyl;
R$^4$ is alkyl, cycloalkyl or

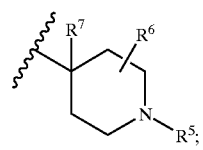

R$^5$ is H, alkyl, —C(O)alkyl, arylcarbonyl, —SO$_2$alkyl, aryl-sulfonyl —C(O)Oalkyl, aryloxycarbonyl, —C(O)NH-alkyl or aryl-aminocarbonyl, wherein the aryl portion is optionally substituted;
R$^6$ is H or alkyl; and
R$^7$ is H, alkyl, hydroxyalkyl or alkoxyalkyl; are muscarinic antagonists useful for treating cognitive disorders such as Alzheimer's disease. Pharmaceutical compositions and methods of treatment are also disclosed

10 Claims, No Drawings

MUSCARINIC ANTAGONISTS

This application claims the benefit of U.S. Provisional Application 06/091,218, filed Jun. 30, 1998.

BACKGROUND OF THE INVENTION

The present invention relates to heteroaromatic derivatives of di-N-substituted piperazines and 1,4-di-substituted piperidines useful in the treatment of cognitive disorders, pharmaceutical compositions containing the compounds, methods of treatment using the compounds, and to the use of said compounds in combination with acetylcholinesterase inhibitors.

Alzheimer's disease and other cognitive disorders have received much attention lately, yet treatments for these diseases have not been very successful. According to Melchiorre et al. (J. Med. Chem. (1993), 36, 3734–3737), compounds that selectively antagonize M2 muscarinic receptors, especially in relation to M1 muscarinic receptors, should possess activity against cognitive disorders. Baumgold et al. (Eur. J. of Pharmacol., 251, (1994) 315–317) disclose 3-α-chloroimperialine as a highly selective m2 muscarinic antagonist.

Logemann et al (Brit. J. Pharmacol. (1961), 17, 286–296) describe certain di-N-substituted piperazines, but these are different from the inventive compounds of the present invention. Furthermore, the compounds of Logemann et al. are not disclosed to have activity against cognitive disorders.

WO 96/26196 discloses benzylpiperidines and piperazines useful as muscarinic antagonists.

SUMMARY OF THE INVENTION

The present invention relates to compounds according to the structural formula I,

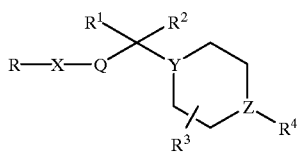

I including all stereoisomers and pharmaceutically acceptable salts and solvates thereof, wherein one of Y and Z is —N— and the other is —N— or —CH—;

X is —O—, —S—, —SO—, —SO$_2$— or —CH$_2$—;

Q is

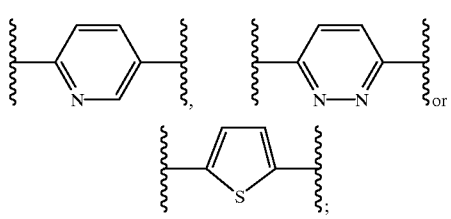

R is (C$_1$–C$_{20}$)alkyl, (C$_3$–C$_{12}$)cycloalkyl, aryl, R$^8$-aryl or heteroaryl;

R$^1$, R$^2$ and R$^3$ are independently selected from the group consisting of H and (C$_1$–C$_{20}$)alkyl;

R$^4$ is (C$_1$–C$_{20}$)alkyl, (C$_3$–C$_{12}$)cyclolalkyl or

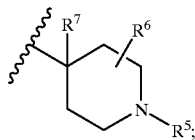

R$^5$ is H, (C$_1$–C$_{20}$)alkyl, —C(O)(C$_1$–C$_{20}$)alkyl, R$^9$-arylcarbonyl, —SO$_2$(C$_1$–C$_{20}$)alkyl, R$^9$-arylsulfonyl —C(O)O(C$_1$–C$_{20}$)alkyl, R$^9$-aryloxy--carbonyl, —C(O)NH—(C$_1$–C$_{20}$)alkyl or R$^9$-arylaminocarbonyzl;

R$^6$ is H or (C$_1$–C$_{20}$)alkyl;

R$^7$ is H, (C$_1$–C$_{20}$)alkyl, hydroxy(C$_1$–C$_{20}$)alkyl or (C$_1$–C$_{20}$)-alkoxy(C$_1$–C$_{20}$)alkyl;

R$^8$ is 1–3 substituents independently selected from the group consisting of H, (C$_1$–C$_{20}$)alkyl, halogen, hydroxy, (C$_1$–C$_{20}$)alkoxy or hydroxy(C$_1$–C$_{20}$)alkyl, or two adjacent R$^8$ groups may be joined to form a (C$_1$–C$_2$)alkylenedioxy group; and R$^9$ is 1–3 substituents independently selected from the group consisting of H, (C$_1$–C$_{20}$)alkyl, halogen, amino or (C$_1$–C$_{20}$)alkylamino.

In a preferred group of compounds Z is N.

In another preferred group of compounds R is R$^8$-substituted phenyl, especially 3,4-methylenedioxyphenyl, 3-methylphenyl, 3-chlorophenyl or 4-methoxyphenyl.

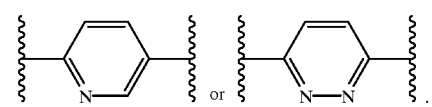

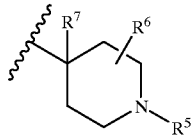

wherein R$^7$ is H or CH$_3$; R$^6$ is H: and R$^5$ is R$^9$-arylcarbonyl, preferably R$^9$-(1-naphthyl)—C(O)—, especially wherein R$^9$ is fluoro, or R$^9$-phenyl-C(O)—, especially wherein R$^9$ is 2-methyl, 2-amino, 2-bromo or 2-chloro.

Another aspect of the invention is a pharmaceutical composition which comprises an effective amount of a compound having structural formula I as defined above in combination with a pharmaceutically acceptable carrier.

Another aspect of the invention is the use of a compound formula I for the preparation of a pharmaceutical composition useful in the treatment of cognitive disorders and neurodegenerative diseases such as Alzheimer's disease.

Another aspect of this invention is a method for treating a cognitive or neurodegenerative disease comprising administering to a patient suffering from said disease an effective amount of a compound of formula I.

DETAILED DESCRIPTION

Except where stated otherwise the following definitions apply throughout the present specification and claims. These definitions apply regardless of whether a term is used by itself or in combination with other terms. Hence the definition of "alkyl" applies to "alkyl" as well as the "alkyl" portions of "alkoxy", etc.

Alkyl represents a straight or branched saturated hydrocarbon chain having 1 to 20 carbon atoms, more preferably 1 to 8 carbon atoms.

Cycloalkyl represents a saturated carbocyclic ring having 3 to 12 carbon atoms.

Halogen represents fluoro, chloro, bromo or iodo.

Aryl represents phenyl or naphthyl.

Heteroaryl refers to 5- to 10-membered single or benzofused aromatic rings comprising 1 to 4 heteroatoms independently selected from the group consisting of —O—, —S— and —N=, provided that the rings do not include adjacent oxygen and/or sulfur atoms. Examples of single-ring heteroaryl groups are pyridyl, oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Examples of benzofused heteroaryl groups are indolyl, quinolyl, benzothienyl (i.e., thianaphthenyl), benzimidazolyl, benzofuranyl, benzoxazolyl and benzofurazanyl. N-oxides of nitrogen-containing heteroaryl groups are also included. 2-, 3-, 5- and 6-positional isomers are contemplated, e.g., 2-pyridyl, 3-pyridyl, 4-pyridyl, 5-pyridyl and 6-pyridyl.

When a variable appears more than once in the structural formula, for example $R^8$, the identity of each variable appearing more than once may be independently selected from the definition for that variable.

Compounds of this invention may exist in at least two stereo configurations based on the asymmetric carbon to which $R^1$ is attached, provided that $R^1$ and $R^2$ are not identical. Also within formula I there are numerous other possibilities for stereoisomerism. All possible stereoisomers of formula I are within the scope of the invention.

Compound of formula I can exist in unsolvated as well as solvated forms, including hydrated forms. In general, the solvated forms, with pharmaceutically acceptable solvents such as water, ethanol and the like, are equivalent to the unsolvated forms for purposes of this invention.

A compound of formula I may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methane-sulfonic and other mineral and carboxylic acids well known to those skilled in the art. The salts are prepared by contacting the free base forms with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia or sodium bicarbonate. The free base forms differ from their respective salt forms somewhat in certain physical properties, such as solubility in polar solvents, but the salts are otherwise equivalent to their respective free base forms for purposes of the invention.

Compounds of formula I may be produced by processes known to those skilled in the art as shown by the following reaction schemes:

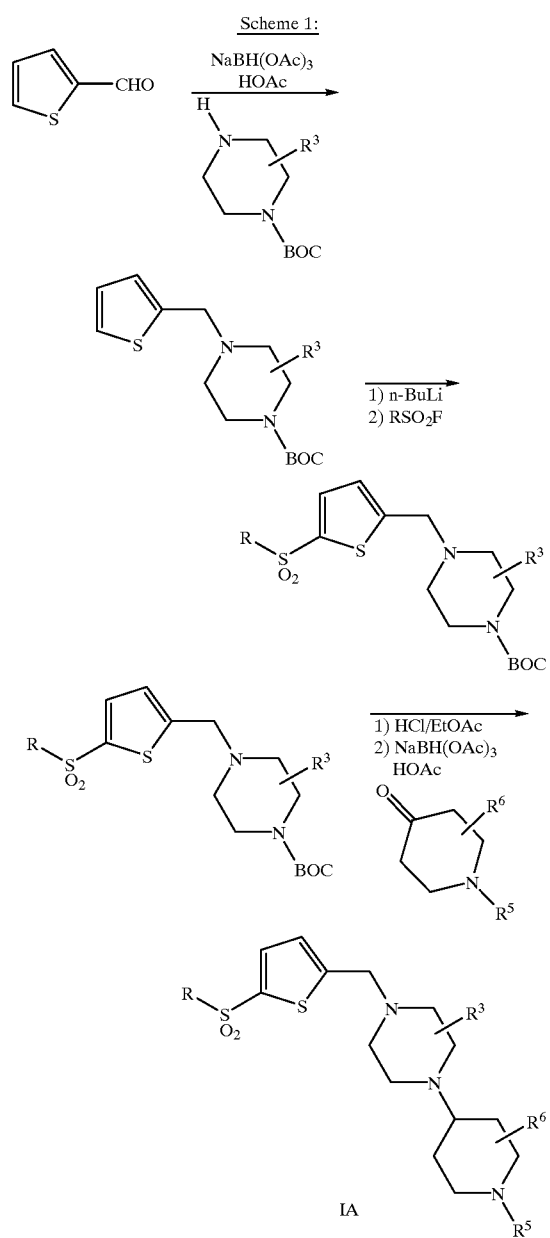

Compounds of formula IA, wherein Y is N, Z is N, Q is thienylidene, X is $SO_2$, $R^4$ is substituted piperidinyl and $R^1$ and $R^2$ are each H, can be prepared by reacting thiophenecarboxaldehyde with a 4—N—BOC-piperazine in the presence of sodium triacetoxy borohydride and acetic acid, followed by reaction with n-butyllithium and R-sulzfonylfluoride. The BOC group is removed with acid and the resultant piperazine is reacted with a piperidone and sodium triacetoxy borohydride and acetic acid to obtain a compound of formula IA.

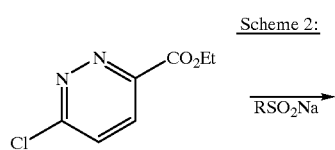

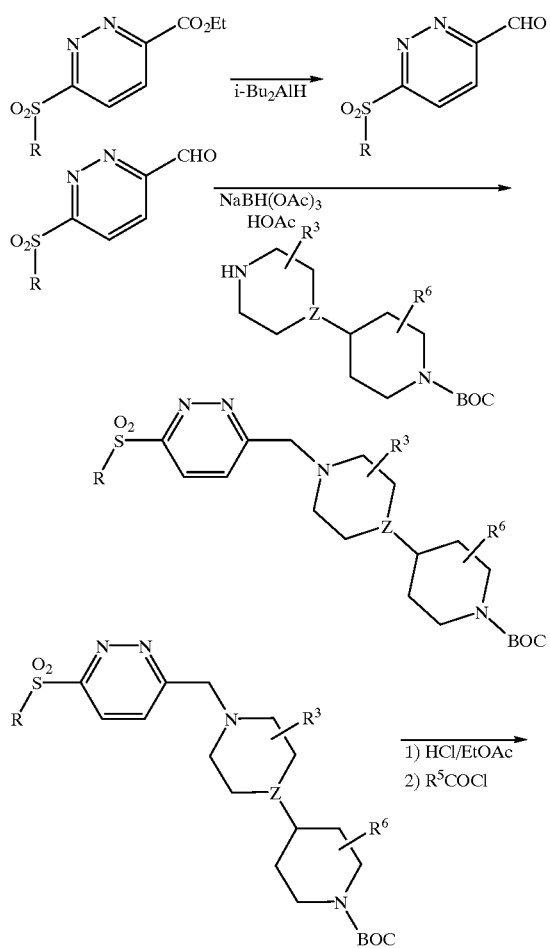

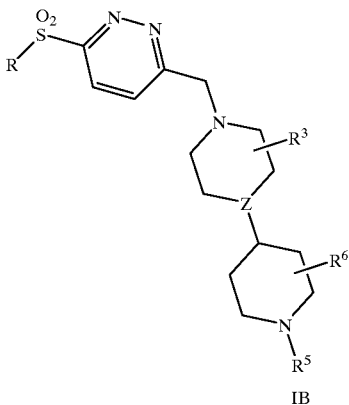

Compounds of formula IB, wherein Y is N, Q is pyridazinylidene, X is $SO_2$, $R^4$ is substituted piperidinyl and $R^1$ and $R^2$ are each H, can be prepared by reacting an alkyl 6-chloropyridazine-3-carboxylate with a compound of the formula $RSO_2Na$, reducing the resultant carboxylate to the aldehyde, and coupling an N-BOC-piperidyl substituted piperidine or piperazine compound to the aldehyde. The BOC protecting group is removed by treatment with acid, and the resultant piperidinyl compound is reacted with a compound of the formula $R^5COCl$ to obtain the desired compound of formula IB.

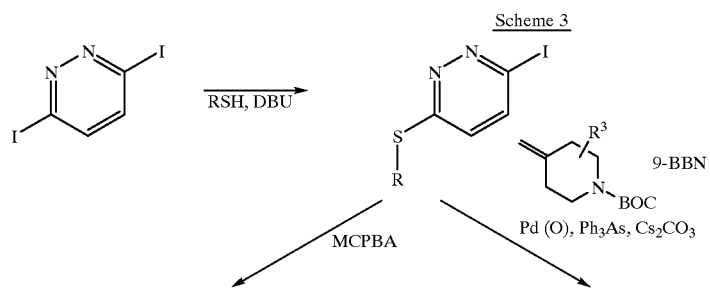

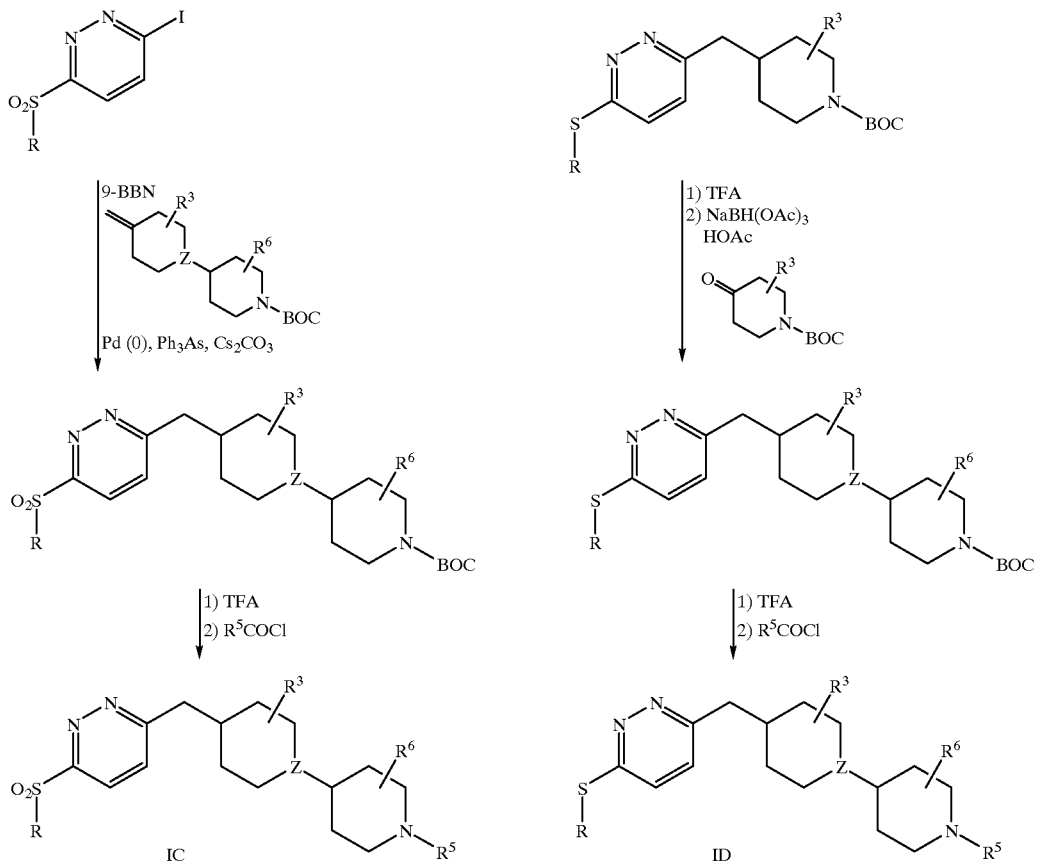

Compounds of formula IC, wherein Y is CH, Q is pyridazinylidene, X is $SO_2$, $R^4$ is substituted piperidinyl and $R^1$ and $R^2$ are each H, can be prepared by reacting 3,6-diiodopyridazine with a compound of the formula RSH in the presence of a strong base such as diazabicycloundecane (DBU), followed by oxidation of the thiol to the sulfonyl by treatment with a reagent such a m-chloroperbenzoic acid. 4-[(4-Methylene)-piperdin-1-yl]-piperidine is treated with a reagent such as 9-borabicyclo[3.3.1]nonane (9-BBN) and the resulting trialkylborane is then reacted with the pyridazine and a palladium (0) catalyst. The BOC protecting group is removed by treatment with acid, and the resultant piperidinyl compound is reacted with a compound of the formula $R^5COCl$ to obtain the desired compound of formula IC.

To prepare compounds of formula ID, wherein Y is CH, Q is pyridazinylidene, X is S, $R^4$ is substituted piperidinyl and $R^1$ and $R^2$ are each H, the R-S-iodopyridazine is reacted with a 4-methylenepiperidine in the presence of a palladium (0) catalyst as described above, followed by reaction with an N—BOC-4-piperidone. The BOC-protecting group is removed and the $R^5$ substituent is attached as described above for preparing compounds of formula IC.

Scheme 4:

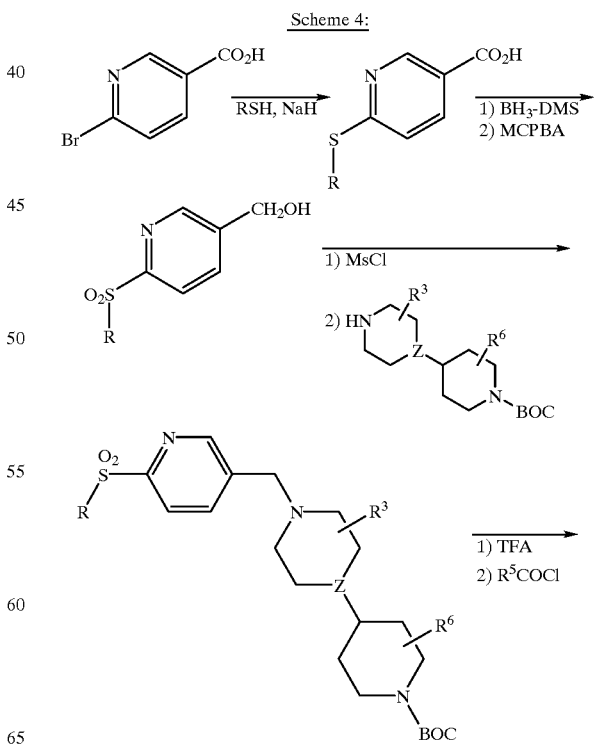

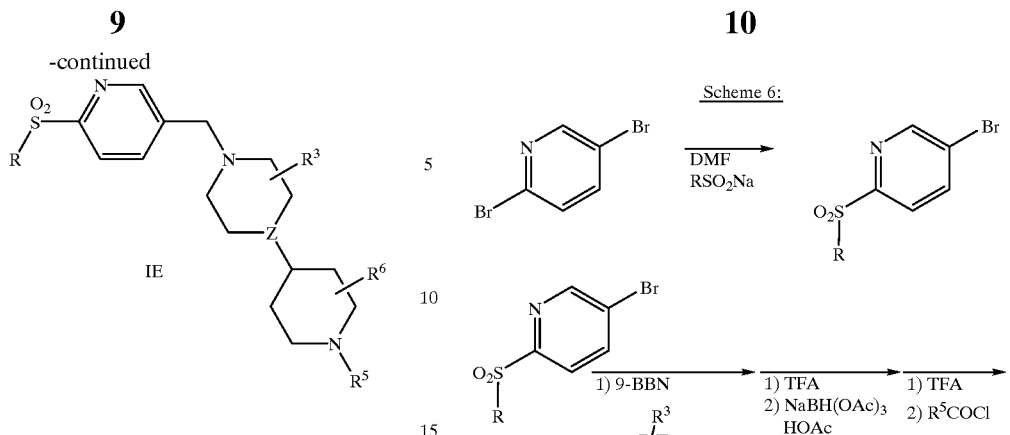

Compounds of formula IE, wherein Y is N, Q is pyridylidene, X is $SO_2$, $R^4$ is substituted piperidinyl and $R^1$ and $R^2$ are each H, can be prepared by reacting a halo-substituted nicotinic acid with a compound of the formula RSH, then reducing the acid to the corresponding alcohol and oxidizing the thiol to the corresponding sulfonyl. The resultant compound is then coupled with an N—BOC-piperidyl substituted piperidine as described for Scheme 2, and the $R^5$ substituent is attached as described for Scheme 3.

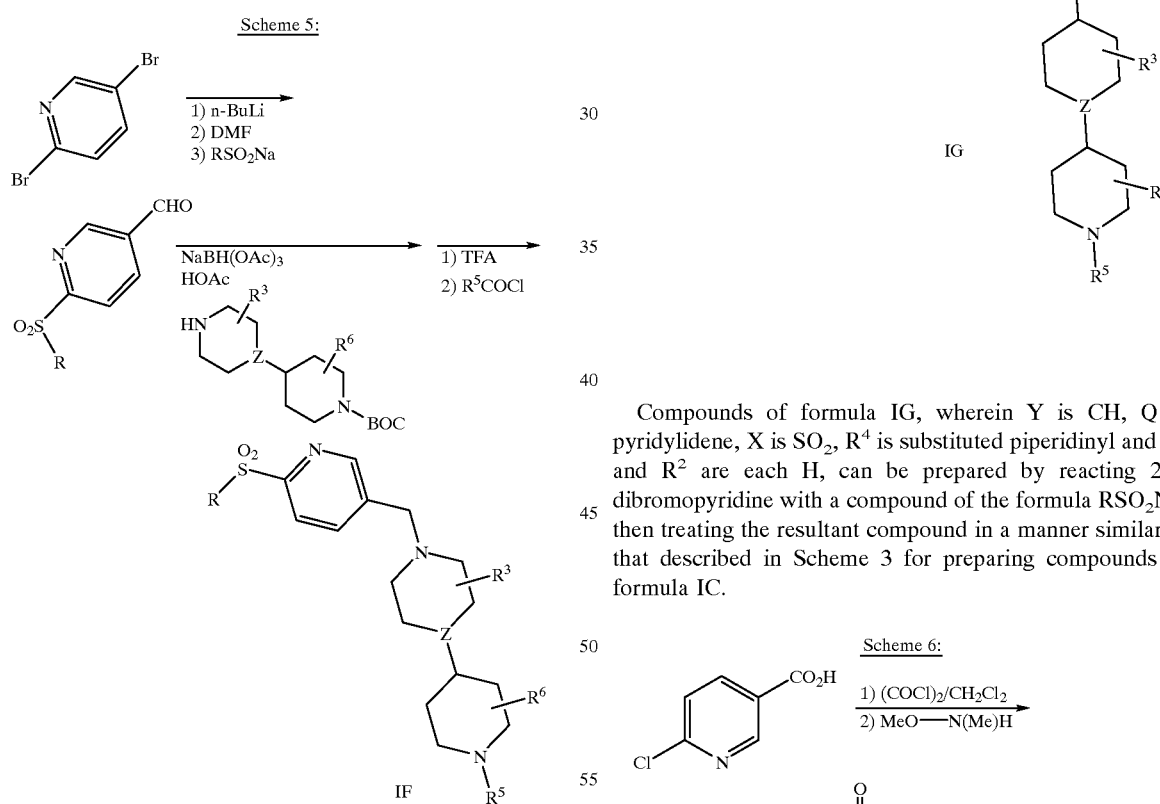

Compounds of formula IF, wherein Y is N, Q is pyridylidene, X is $SO_2$, $R^4$ is substituted piperidinyl and $R^1$ and $R^2$ are each H, can be prepared by reacting 2,5-dibromopyridine with a compound of the formula $RSO_2Na$ and n-butyllithium, followed by coupling with an N—BOC-piperidyl substituted piperidine or piperazine, removing the BOC protecting group as described in Scheme 2 and reacting with $R^5COCl$ as described in Scheme 3 to obtain the desired compound.

Compounds of formula IG, wherein Y is CH, Q is pyridylidene, X is $SO_2$, $R^4$ is substituted piperidinyl and $R^1$ and $R^2$ are each H, can be prepared by reacting 2,5-dibromopyridine with a compound of the formula $RSO_2Na$, then treating the resultant compound in a manner similar to that described in Scheme 3 for preparing compounds of formula IC.

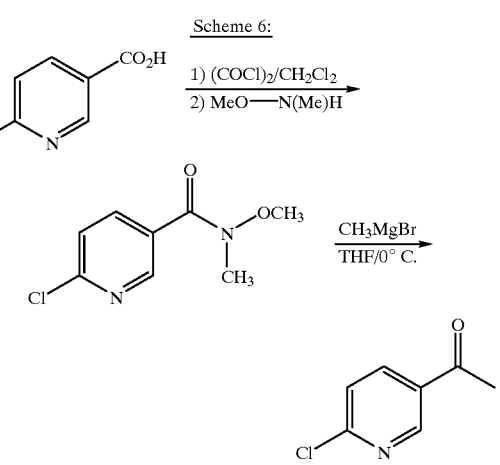

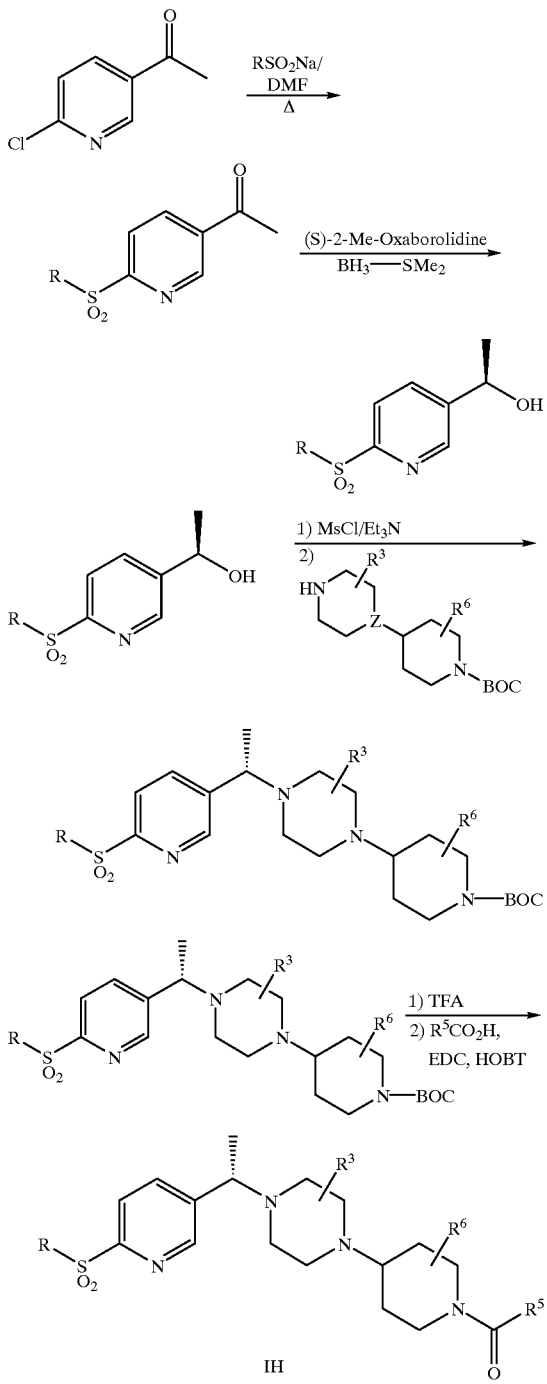

Compounds of formula IH, , wherein Y is N, Q is pyridylidene, X is $SO_2$, $R^4$ is substituted piperidinyl, $R^1$ is methyl and $R^2$ is H, are prepared by converting 6-chloronicotinic acid to the corresponding chloro-ketone via the Weinreb amide. The chloro-ketone is reacted with $RSO_2Na$ in hot DMF, followed by enantioselective reduction using the (S)-2-methyl oxaborolidine catalyst and borane-methyl sulfide to furnish the chiral alcohol which is enriched in the R-enantiomer. The mesylate derived from the alcohol is reacted with a piperazino piperidine in refluxing acetonitrile, and removal of the BOC protecting group followed by coupling to various aromatic acids ($R^5CO_2H$) under standard conditions provides the target compounds IH.

The above reactions may be followed if necessary or desired by one or more of the following steps; (a) removing any protective groups from the compound so produced; (b) converting the compound so- produced to a pharmaceutically acceptable salt, ester and/or solvate; (c) converting a compound in accordance with formula I so produced to another compound in accordance with formula I, and (d) isolating a compound of formula I, including separating stereoisomers of formula I.

Based on the foregoing reaction sequence, those skilled in the art will be able to select starting materials needed to produce any compound in accordance with formula I.

The compounds of formula I exhibit selective m2 and/or m4 muscarinic antagonizing activity, which has been correlated with pharmaceutical activity for treating cognitive disorders such as Alzheimers disease and senile dementia.

The compounds of formula I display pharmacological activity in test procedures designated to indicate m1 and m2 muscarinic antagonist activity. The compounds are non-toxic at pharmaceutically therapeutic doses. Following are descriptions of the test procedures.

MUSCARINIC BINDING ACTIVITY

The compound of interest is tested for its ability to inhibit binding to the cloned human m1, m2, m3, and m4 muscarinic receptor subtypes. The sources of receptors in these studies were membranes from stably transfected CHO cell lines which were expressing each of the receptor subtypes. Following growth, the cells were pelleted and subsequently homogenized using a Polytron in 50 volumes cold 10 mM Na/K phosphate buffer, pH 7.4 (Buffer B). The homogenates were centrifuged at 40,000×g for 20 minutes at 4° C. The resulting supernatants were discarded and the pellets were resuspended in Buffer B at a final concentration of 20 mg wet tissue/ml. These membranes were stored at −80° C. until utilized in the binding assays described below.

Binding to the cloned human muscarinic receptors was performed using $^3$H-quinuclidinyl benzilate (QNB) (Watson et al., 1986). Briefly, membranes (approximately 8, 20, and 14 μg of protein assay for the m1, m2, and m4 containing membranes, respectively) were incubated with $^3$H-QNB (final concentration of 100–200 pM) and increasing concentrations of unlabeled drug in a final volume of 2 ml at 25° C. for 90 minutes. Non-specific binding was assayed in the presence of 1 μM atropine. The incubations were terminated by vacuum filtration over GF/B glass fiber filters using a Skatron filtration apparatus and the filters were washed with cold 10 mM Na/K phosphate butter, pH 7.4. Scintillation cocktail was added to the filters and the vials were incubated overnight. The bound radioligand was quantified in a liquid scintillation counter (50% efficiency). The resulting data were analyzed for $IG_{50}$ values (i.e. the concentration of compound required to inhibit binding by 50%) using the EBDA computer program (McPherson, 1985). Affinity values ($K_i$) were then determined using the following formula (Cheng and Prusoff, 1973);

$$K_i = \frac{IC_{50}}{1 + \left[\frac{\text{concentration of radioligand}}{\text{affinity }(K_D)\text{ of radioligand}}\right]}$$

Hence, a lower value of $K_i$ indicates greater binding affinity.

To determine the degree of selectivity of a compound for binding the m2 receptor, the $K_i$ value for m1 receptors was divided by the $K_i$ value for m2 receptors. A higher ratio indicates a greater selectivity for binding the m2 muscarinic receptor.

For the compounds of this invention, the following range of muscarinic antagonistic binding activity was observed (not all compounds were tested for m3 and m4 binding activity):

m1: 96 nM to 1860 nM m2: 1.5 nM to about 1400 nM, preferably 1.5 nM to about 600 nM m3: 59 nM to 2794 nM m4: 28 nM 638 nM A preferred compound of this invention, the compound of Example 39, has an average m1 antagonist binding activity of 917 and an average m2 antagonist binding activity of 1.5.

For preparing pharmaceutical compositions from the compounds of formula I, pharmaceutically acceptable, inert carriers are admixed with the active compounds. The pharmaceutically acceptable carriers may be either solid or liquid. Solid form preparations include powders, tablets, dispersible granules, capsules, cachets and suppositories. A solid carrier can be one or more substances which may also act as diluents, flavoring agents, solubilizers,. lubricants, suspending agents, binders or tablet disintegrating agents; it may also be an encapsulating material.

Liquid form preparations include solutions, suspensions and emulsions. As an example may be mentioned water or water-propylene glycol solutions for parenteral injection.

Also included are solid form preparations which are intended to be converted, shortly before use, to liquid form preparations for either oral or parentertal administration. Such liquid forms include solutions, suspensions and emulsions. These particular solid form preparations are most conveniently provided in unit dose form and as such are used to provide a single liquid dosage unit.

The invention also contemplates alternative delivery systems including, but not necessarily limited to, transdermal delivery. The transdermal compositions can take the form of creams, lotions and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation such as packeted tablets, capsules and powders in vials or ampules. The unit dosage form can also be a capsule, cachet or tablet itself, or it may be the appropriate number of any of these in a packaged form.

The quantity of active compound in a unit dose preparation may be varied or adjusted from 1 mg to 100 mg according to the particular application and the potency of the active ingredient and the intended treatment. This would correspond to a dose of about 0.001 to about 20 mg/kg which may be divided over 1 to 3 administrations per day. The composition may, if desired, also contain other therapeutic agents.

The dosages may be varied depending on the requirement of the patient, the severity of the condition being treating and the particular compound being employed. Determination of the proper dosage for a particular situation is within the skill of those in the medical art. For convenience, the total daily dosage may be divided and administered in portions throughout the day or by means providing continuous delivery.

The invention disclosed herein is exemplified by the following examples which should not be construed to limit the scope of the disclosure. Alternative mechanistic pathways and analogous structures may be apparent to those skilled in the art. As used herein, tetrahydrofuran is THF, dimethylformamide is DMF, ethyl acetate is EtOAc, trifluoroacetic acid is TFA, dimethylsulfoxide is DMSO, m-chloro-perbenzoic acid is MCPBA, triethyl amine is $Et_3N$, diisopropyl ethylamine is $iPr_2EtN$, 9-borabicyclo [3.3.1]-nonane is 9-BBN, and 1,1'-bis(diphenyl-phosphino)-ferrocene palladium (II) chloride is $Pd(dppf)Cl_2$. In the examples, Ar in the structures is 3-methylphenyl; $Ar^1$ is 4-methyoxyphenyl.

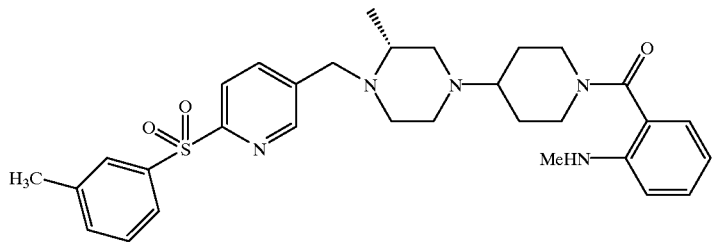

Reaction Scheme:

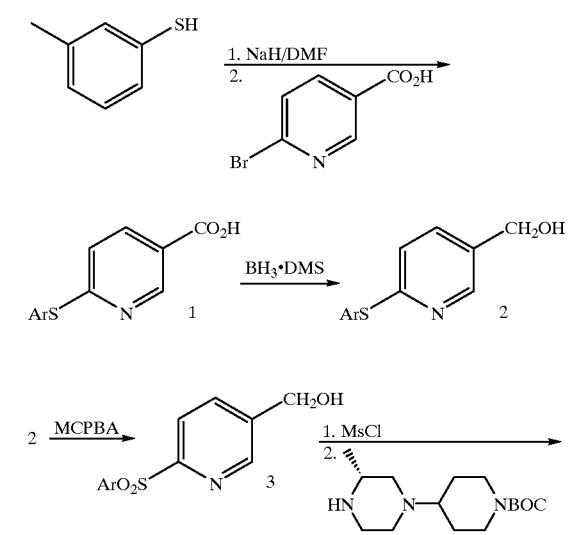

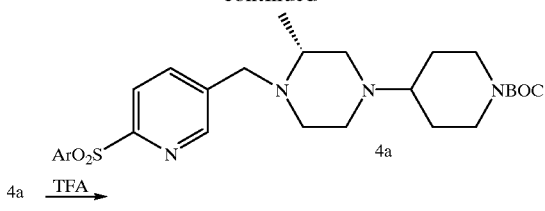

4a  TFA→

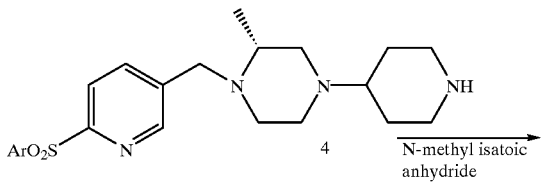

4  N-methyl isatoic anhydride →

Ex. 1

Step 1A: To a cooled (0° C.) mixture of DMF (25 mL) and NaH (1.00 g of a 60% suspension in oil) was added, slowly dropwise, m-toluene thiol (3.10 g). After the addition was complete, the cooling bath was removed, the resulting mixture was stirred for 1 h at room temperature (RT), 6-bromo-nicotinic acid (5.00 g) was added all at once and the resulting mixture was heated at reflux for 6 h. After cooling to RT, the mixture was poured into cold water (250 mL) and the resulting solid was collected, washed with water and dried to give the desired product 1 (4.91 g) in 80% yield.

To a solution of sulfide 1 (0.50 g) and THF (2 mL) was added BH$_3$DMS (0.61 mL), dropwise. The resulting solution was stirred for 1 h at RT, diluted with EtOAc and ice and stirred for 5 min. The pH was adjusted to 11 with 2 N NaOH and the resulting mixture was extracted with EtOAc (3×10 mL). The EtOAc extracts were dried with brine, then over MgSO$_4$, filtered and evaporated to give a light colored foam 2 (0.44 g), which was used without further purification.

Step 1B: To a cooled (0° C.) solution of 2 and CH$_2$Cl$_2$ was added MCPBA (671 mg of technical grade) in three portions over 10 min. After warming to RT and stirring for 12 h, the resulting mixture was diluted with CH$_2$Cl$_2$ (5 mL) and MCPBA (300 mg) was added. After 4 h at RT, the resulting mixture was diluted with CH$_2$Cl$_2$, washed successively with cold 1 N NaOH, water and brine and dried over MgSO$_4$. After filtration and evaporation, the crude oil was purified by preparative plate chromatography (2000 μM plate; silica adsorbent; 2:1 EtOAc:hexane eluant) to give the product 3 as a white solid (0.22 g).

Step 2: To a cooled (0° C.) solution of sulfone 3 (0.20 g), CH$_2$Cl$_2$ (7.5 mL) and Et$_3$N (0.13 mL) was added CH$_3$SO$_2$Cl (0.061 mL). The resulting solution was stirred for 5 min at 0° C. and 30 min at RT and then washed successively with water, 1 N NaOH and brine and dried over MgSO$_4$. After filtration and evaporation, the resulting oil was dissolved in CH$_3$CN (0.68 mL) and iPr$_2$EtN (0.14 mL) and the piperazine (0.29 g) was added. The resulting solution was stirred for 12 h at which time CH$_3$CN (0.5 mL) was added and stirring was continued for 2 days. The CH$_3$CN was removed in vacuo and the resulting crude mixture was partitioned between CH$_2$Cl$_2$ and water. The pH was adjusted to 11 with 2 N NaOH, the CH$_2$Cl$_2$ layer was removed and the aqueous layer extracted with CH$_2$Cl$_2$ (3×3 mL). The combined organic extracts were dried with brine and over MgSO$_4$, filtered and evaporated to give a crude gum which was purified by preparative plate chromatography (2×2000 μM plate; silica adsorbent; 95:5 EtOAc:Et$_3$N eluant) to give the product 4a as a foam (0.29 g) in 82 % yield. HRMS: calc'd: M.H$^+$: C$_{28}$H$_{41}$N$_4$O$_4$S: 529.2849; measured: 529.2840.

Step 3: To a cooled (0° C.) solution of 4a (0.27 g) and CH$_2$Cl$_2$ (2.1 mL) was added TFA (0.42 mL) and water (9 μL). The resulting solution was stirred at RT for 2 h; the volatile materials were removed in vacuo; CH$_2$Cl$_2$ (20 mL) was added; the pH was adjusted to 11 with 10% NaOH and the organic layer was removed. After drying (with brine and MgSO$_4$) and evaporation, the product 4 was collected as a white foam (0.16 g) in 71% yield.

Step 4: The product of Step 3, 4 (29 mg), was mixed with CH$_3$CN (0.4 mL), iPr$_2$EtN (0.15 mL) and N-methyl isatoic anhydride (48 mg). After stirring for 2 days at RT, the resulting mixture was diluted with EtOAc (15 mL) and washed with cold water, brine and dried over MgSO$_4$, then filtered and evaporated to give a crude solid which was further purified by preparative plate chromatography (500 μM plate; silica adsorbent; 95:5 EtOAc:Et$_3$N eluant) to give the product as a foam (28 mg) in 75% yield. HRMS (as the HCl): calc'd: M.H$^+$: C$_{31}$H$_{40}$N$_5$O$_3$S: 562.2852; measured: 562.2850; mp (HCl): 144–148° C. (with decomposition).

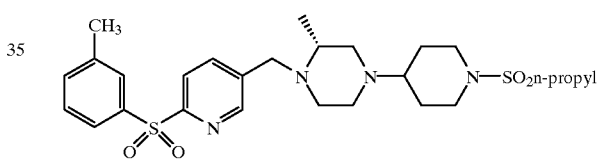

The intermediate 4 (29 mg) from Example 1 was dissolved in CH$_2$Cl$_2$ (1.0 mL) and 2.0 M Na$_2$CO$_3$ (0.2 mL) was added. The resulting mixture was cooled to 0° C. and CH$_3$(CH$_2$)$_2$SO$_2$Cl (7.62 μL) was added. The mixture was stirred for 5 min at 0° C. and 15 min at RT then MgSO$_4$ was added. The CH$_2$Cl$_2$ layer was removed and the solids were extracted with CH$_2$Cl$_2$ (3×3 mL), the CH$_2$Cl$_2$ extracts were combined, dried with MgSO$_4$, filtered and evaporated to give a crude foam which was purified by preparative plate chromatography (500 μM plate; silica adsorbent; 95:5 EtOAc:Et$_3$N eluant) to give the product as a foam (33 mg) in 90% yield. HRMS (as the HCl): calc'd: M.H$^+$: C$_{26}$H$_{38}$N$_4$O$_4$S$_2$: 535.2413; measured: 535.2405; mp (HCl): 146–150° C. (with decomposition).

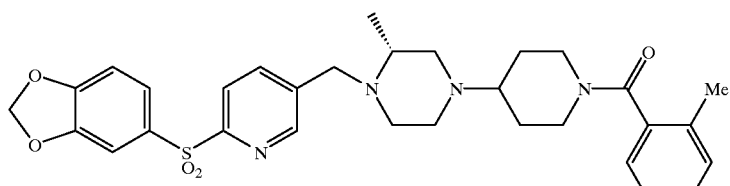

Reaction Scheme:

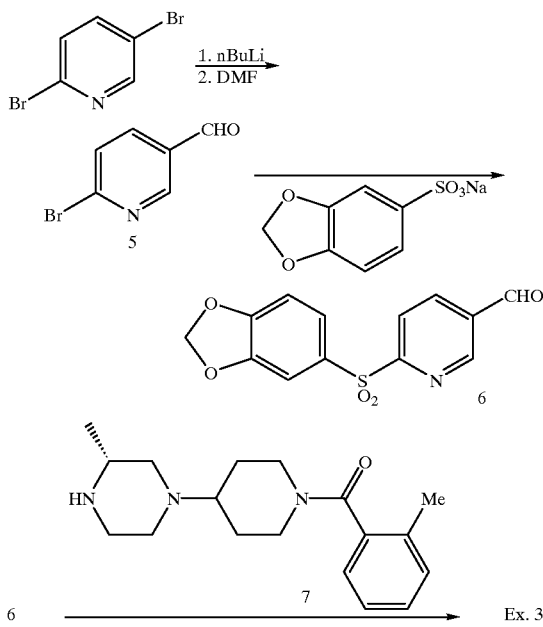

Step 1: To a cooled (−90° C.) solution of 2,5-dibromopyridine (10 g) and THF (264 mL) was added, dropwise, nBuLi (16.9 mL of a 2.5 M solution in hexanes) and the resulting solution was stirred for 5 min. DMF (3.27 mL) was added dropwise and the resulting solution was warmed to −50° C. and stirred for 15 min at that temperature. The reaction solution was poured onto ice and extracted with EtOAc (3×75 mL). The combined EtOAc extracts were dried over MgSO$_4$, filtered and evaporated to give 7.8 g of crude material which was purified by silica gel chromatography (4:1 hexane:EtOAc as eluant). After combining the desired fractions and evaporating the solvents, the desired aldehyde 5 was isolated as a solid (0.89 g) in 11% yield.

Step 2: A mixture of 5 (0.20 g), DMSO (1.0 mL) and 3,4-methylene dioxy benzene sulfinate, sodium salt (0.19 g) was heated at 40° C. for 21 h then cooled and poured into water (10 mL). The resulting solution was made basic (pH=11) with 2 N NaOH and extracted with EtOAc (3×5 mL). The combined extracts were dried with brine and MgSO$_4$, filtered and evaporated to give a crude oil which was purified by silica gel chromatography (2:1 hexane:EtOAc eluant). The desired fractions were combined and evaporated to give the product 6 (0.10 g) in 33% yield.

Step 3: To a solution of 6 (0.10 g), the piperazine 7 (0.23 g) and CH$_2$Cl$_2$ (2.5 mL) was added NaB(OAc)$_3$H (0.11 g) and the resulting solution was stirred for 1.5 h. The reaction was diluted with CH$_2$Cl$_2$ and made basic with 2 N NaOH. The CH$_2$Cl$_2$ layer was removed and the aqueous layer was extracted with CH$_2$Cl$_2$ (2×5 mL). The organic extracts were combined, washed with water, brine and dried over MgSO$_4$, then filtered and evaporated to give a crude oil which was purified by preparative plate chromatography (2000 μM plate; silica adsorbent; 1:1 CH$_2$Cl$_2$:

acetone eluant) to give the product as a foam (95 mg) in 47% yield. mp(HCl): decompostion above 225° C.

Example 4

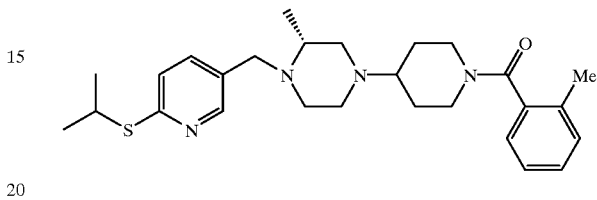

Reaction scheme:

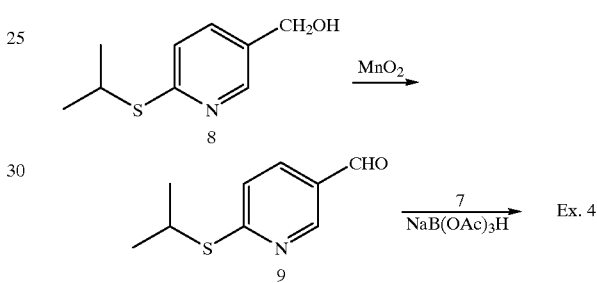

Step 1: The carbinol intermediate 8 was prepared by the method outlined for Step 1A of Example 1, but m-toluene thiol was replaced with iso-propyl thiol.

Step 2: The carbinol intermediate 8 (50 mg) was dissolved in CHCl$_3$ (1.0 mL) and MnO$_2$ (165 mg) was added. The resulting mixture was heated at reflux for 2 days and the solid reaction mixture was then cooled, taken up in CHCl$_3$ (10 mL) and filtered through Celite. The solids were washed with CHCl$_3$ (3×10 mL), the organic extracts were combined, dried over MgSO$_4$, filtered and evaporated to give the desired aldehyde 9 (42 mg) in 86% yield.

Step 3: 9 was subjected to the same reaction conditions as outlined in Example 3, Step 3, using piperazine intermediate 7, to give the title compound (0.12 g) in 50% yield. mp(HCl): decomposition above 197° C.

Example 5

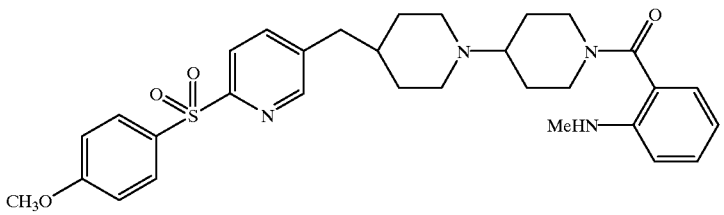

Reaction scheme:

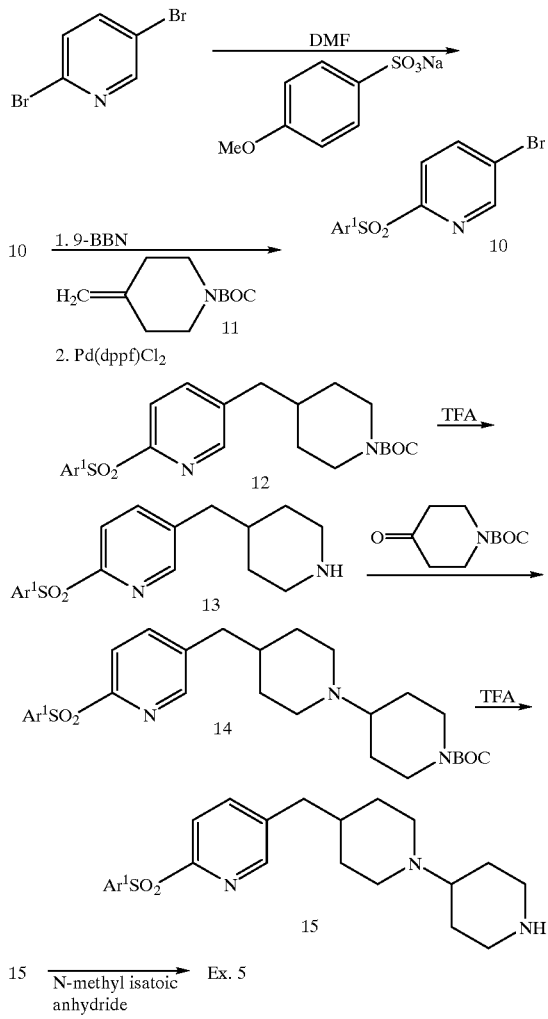

Step 1: A mixture of 2,5-dibromopyridine (3.7 g), para-methoxy benzene sulfinate, sodium salt (3.0 g) and DMF (8.0 mL) was heated at reflux for 48 h, cooled and partitioned between water and EtOAc. The aqueous layer was checked to be basic (pH>8) and was extracted with EtOAc (2×75 mL). The organic extracts were combined, washed with water and brine and dried over $MgSO_4$. After filtration and evaporation, the crude solid (3.5 g) was chromatographed on silica gel (gradient: 8:1 hexanes: EtOAc; 4:1 hexanes:EtOAc; 1:1 hexanes:EtOAc) to give, after evaporation of the appropriate fractions, 10 (0.27 g) in 5.3% yield. mp: 104–107 ° C.

Step 2: To a degassed, cooled (0° C.) sample of 11 (1.7 g) was added 9-BBN (17.5 mL of a 0.5 M in THF). The cooling bath was removed and the solution was stirred for 1.5 h at RT. The resulting solution was added, at RT, to a mixture of the sulfone 10 (0.27 g), Pd(dppf)$Cl_2$ (20 mg), triphenyl arsine (25 mg), DMF (2.0 mL), water (0.18 mL) and $Cs_2CO_3$ (0.33 g). The resulting mixture was heated at 60° C. for 3 h 45 min. After cooling to RT and pouring into water, the pH was adjusted to 11 with 10% NaOH and mixture was extracted with EtOAc (3×25 mL). The combined organic extracts were dried with brine and $MgSO_4$, filtered and evaporated to give a crude which was further purified by preparative plate chromatography (2000 μM plate; silica adsorbent; 1:1 EtOAc:hexanes eluant) to give the product 12 as a white foam (0.28 g) in 77% yield.

Step 3: 12 was treated as described in Example 1, Step 3. The product 13 was isolated as a foam (0.11 g) in 82% yield.

Step 4: 13 was treated as described in Example 3, Step 3, except one equivalent of acetic acid was added and N—BOC-piperidone was used as the carbonyl component. After work up, the crude was further purified by preparative plate chromatography (2000 μM plate; silica adsorbent; 95:5 EtOAc:$Et_3N$ eluant) to give 14 as an oil (0.21 g).

Step 5: 14 was treated as described in Example 1, Step 3, to give 15 as a white foam (53 mg) in 41% over two steps. HRMS: calc'd: $MH^+$: $C_{23}H_{22}N_3O_3S$: 430.2164; measured: 430.2160.

Step 6: 15 was treated as described in Example 1, Step 4 and was purified by preparative plate chromatography (500 μM plate; silica adsorbent; 95:5 EtOAc:$Et_3N$ eluant) to give the title compound as an oil (33 mg) in 96% yield. mp(HCl): 108–110° C. (with decomposition).

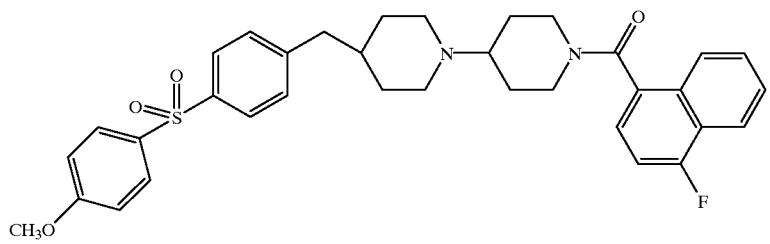

The intermediate 15 from Example 5, Step 6 was treated as described in Example 2, except the sulfonyl chloride was replaced with 4-fluoro-naphthoyl chloride and the crude was purified by preparative plate chromatography (500 μM plate; silica adsorbent; 95:5 EtOAc:$Et_3N$ eluant) to give the title compound as an oil (33 mg) in 96% yield. mp(HCl): decomposition above 184° C.

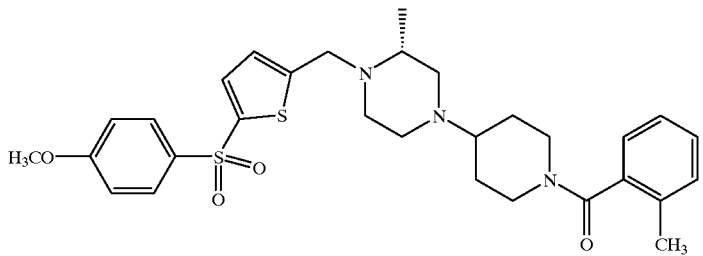

Reaction scheme:

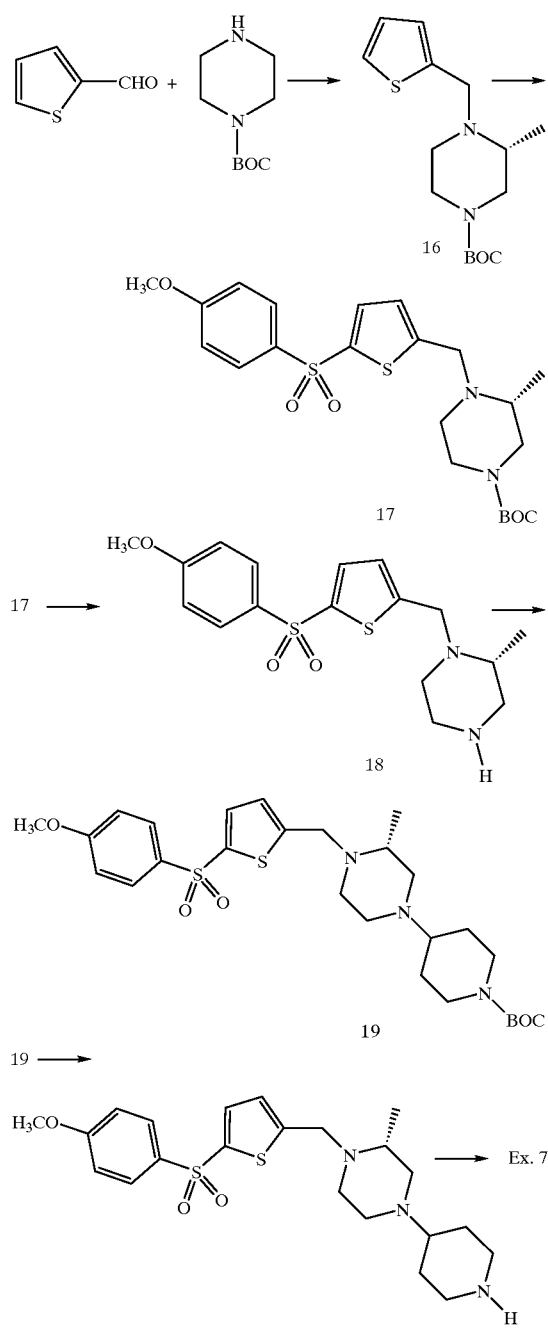

Step 1: To CH₂Cl₂ (50 mL), add 4-N—BOC-2-(R)-methypiperazine (1 g, 4.9 mmol), thiophene-2-carboxaldehyde (0.46 mL), NaBH(OAc)₃ (1.5 g, 7.5 mmol) and acetic acid (0.25 mL), and stir overnight at RT. Add CH₂Cl₂ (100 mL) and wash with saturated NaHCO₃ and brine. The organic phase was dried over Na₂SO₄ and concentrated on a rotary evaporator. The crude product 16 was purified on a silica column eluted with EtOAc.

Step 2: 16 was dissolved in THF (15 mL), then cooled in a dry ice/acetone bath where n-BuLi (0.64 mL, 2.5 M) was added dropwise. After 15 min the temperature was raised to 0° C., stirred for 30 min, then recooled to −78° C. where 4-methoxybenzenesulfonyl fluoride (0.3 g, 1.6 mmol) was added. After 10 min, the temperature was raised to 0° C. for 15 min, then to RT for 15 min. After quenching with saturated NaHCO₃, EtOAc was added and the organic phase washed with brine and dried over Na₂SO₄. The crude product 17 was purified on a silica column using 2:1 hexane:EtOAc.

Step 3: 17 (0.22 g) was dissolved in EtOAc (4 mL) and 6 N HCl (0.8 mL) was added with vigorous stirring. After 2 h the reaction was neutralized with saturated NaHCO₃ solution. CH₂Cl₂ (50 mL) was added and the organic phase separated and dried over NaHCO₃. After concentration on a rotary evaporator, the crude product 18 was used without purification.

Step 4: N—BOC-piperidone (0.09 g, 0.43 mmol), 18 (0.16 g, 0.43 mmol), NaBH(OAc)₃ (0.14 g, 0.65 mmol) and acetic acid (0.025 mL) were added to CH₂Cl₂ (5 mL), and the mixture was stirred overnight at RT. CH₂Cl₂ (10 mL) was added and washed with saturated NaHCO₃, and brine. The organic phase was dried over Na₂SO₄ and concentrated on a rotary evaporator. The crude product 19 was purified on a silica column using EtOAc as eluent.

Step 5: 19 (0.2 g) was dissolved in EtOAc (3 mL) and 6 N HCl (0.5 mL) added with vigorous stirring. After 2 h, the reaction was neutralized with saturated NaHCO₃ solution. CH₂Cl₂ (15 mL) was added and the organic phase separated and dried over NaHCO₃. After concentration on a rotary evaporator the crude product 20 was used without purification.

Step 6: 20 (0.03 g) was dissolved in CH₂Cl₂ (1 mL) followed by addition of Et₃N (0.011 mL), and o-toluoyl chloride (0.007 mL). After 1 h at RT the solution was transferred directly to a prep. TLC plate and eluted with EtOAc. The major UV band (Rf=0.1) was collected and extracted with 10% CH₃OH/EtOAc. Filtration and evaporation gave the purified material. The HCl salt was prepared by dissolving the product in a minimum amount of EtOAc followed by additon of dry HCl/ether. The precipitate was collected with a centrifuge, washed with ether and dried under vacuum to obtain the title compound. mp 190–192° C. (decomposition).

Example 8

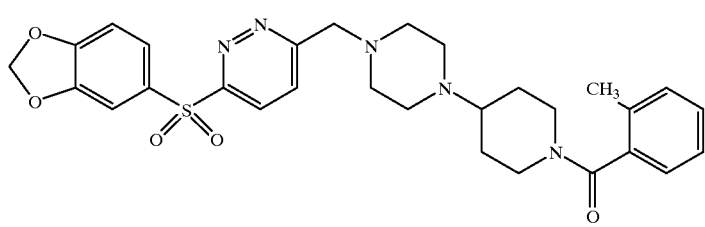

Reaction scheme:

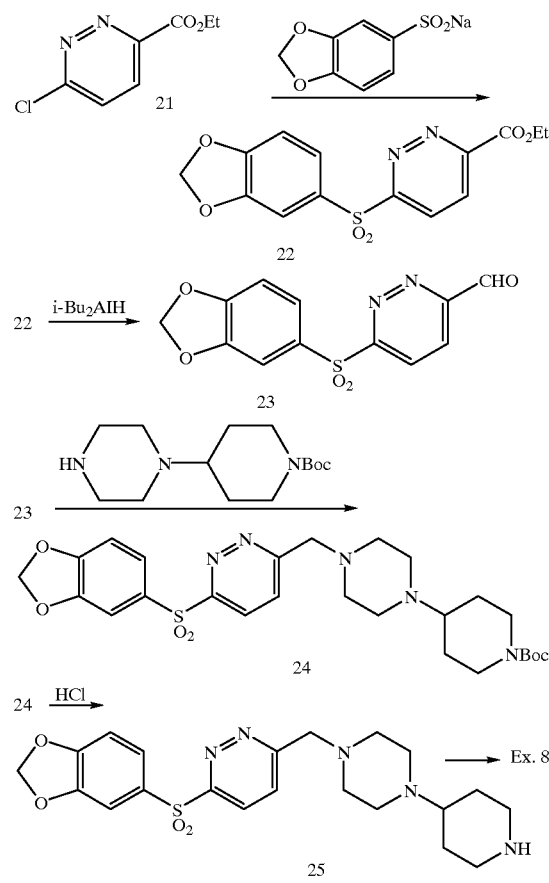

Step 1: Heat a mixture of ethyl 6-chloropyridazine-3-carboxylate 21 (1.8 g), sodium (3,4-methylenedioxy)-benzenesulfonate (2 g) and DMSO (20 mL) at 120–125° C. for 8 h. Cool and add to water (100 mL) stir 10 min. collect, wash well with water and dry at RT in high vacuum to give compound 22 as a white solid (2.0 g), mp 153–155° C.

Step 2: To an ice-cooled solution of compound 22 (0.6 g) in dry THF (40 mL) add 1 M diisobutylaluminum hydride in toluene (3.6 mL), stir for 5 min., add $CH_2Cl_2$ (100 mL) and then excess iced water. Stir and add 2N HCl (20 mL) to dissolve the solids. Extract with $CH_2Cl_2$, dry over $MgSO_4$ and filter on a small pad of silica gel, washing with 20% EtOAc in $CH_2Cl_2$. Evaporate to obtain the aldehyde 23 (0.42 g) as a yellow foam, suitable for the next step.

Step 3: Stir a mixture of compound 23 (0.42 g), 1-(1-tertbutoxy-carbonyl-piperidin-4-yl)-piperazine (0.42 g) and $NaBH(OAc)_3$ (0.42 g) in $CH_2Cl_2$ (30 mL) at RT for 6 h. Wash with 1 N aqueous NaOH solution, dry over $MgSO_4$ and evaporate. Isolate the product by silica gel chromatography with a gradient of EtOAc in $CH_2Cl_2$, and evaporate the pure fractions to obtain compound 24 as a white foam (0.58 g).

Step 4: Stir the product of Step 3 in EtOAc (20 mL) and conc. HCl (5 mL) for 2 h. at RT. Basify with excess 2N NaOH with ice cooling, extract with several portions of $CH_2Cl_2$, dry over $K_2CO_3$ and evaporate to obtain the amine 25 as a pale yellow foam (0.35 g).

Step 5: Stir for 20 h. at RT a mixture of compound 25 (0.04 g), o-toluoyl chloride (0.04 g), $CH_2Cl_2$ (10 mL) and 1N aqueous NaOH (10 mL). Separate the organic phase, dry and evaporate. Dissolve the residue in $CH_2Cl_2$ (1 mL) and add to ether (15 mL) containing HCl-dioxan (4M; 0.25 mL). Centrifuge and wash by suspension-cenrtifugation 3× with ether, then dry under a nitrogen stream, and finally at high vac./RT to give the hydrochloride of the title compound as a cream powder (0.035 g), mp 195–198° C. with decomposition.

Example 9

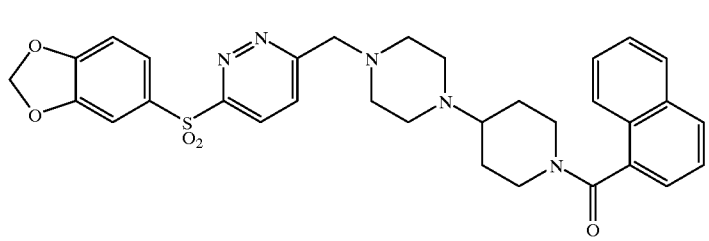

Use the procedure of Example 8, replacing the toluoyl chloride with -1-naphthoyl chloride (0.05 g) to obtain the final hydrochloride (0.042 g) of the title compound as a white powder, mp 175–180° C. with decomposition.

Example 10

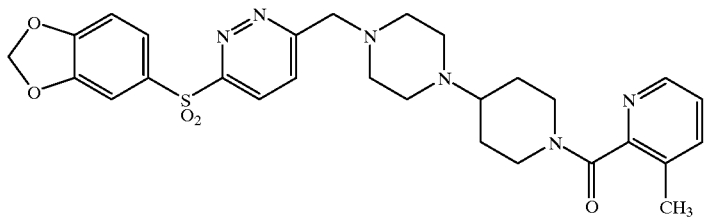

Stir for 20 h. at RT a mixture of compound 25 from Example 8 (0.058 g), DMF (2 mL), iPr$_2$EtN (0.1 mL), hydroxybenzotriazole (HOBT) (0.038 g), 3-methylpicolinic acid hydrochloride (0.036 g) and N-ethyl-N'-(dimethylaminopropyl)-carbodiimide hydrochloride (EDCI) (0.055 g). Extract in EtOAc-aq. NaHCO$_3$, wash with several portions of 5% aq. NaCl, dry over MgSO$_4$, evaporate and pump at high vacuum to remove any residual DMF. Precipitate the HCl salt as described in Example 8 to obtain the title compound (0.035 g) as a hygroscopic powder with a broad melting range.

Example 11

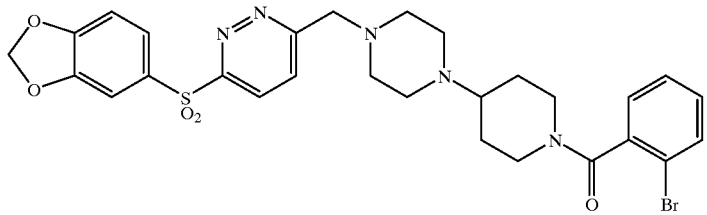

Use the procedure of Example 8, but replace the toluoyl chloride with 2-bromobenzoyl chloride (0.05 g) to obtain the hydrochloride of the title compound (0.040 g) as a white powder, mp 198–203° C. with decomposition.

Example 11

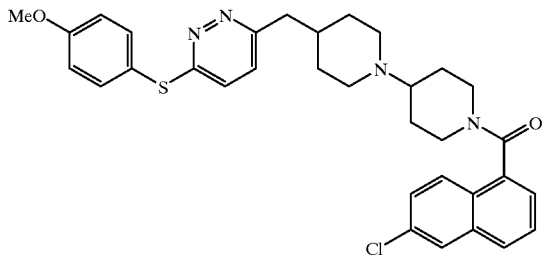

Reaction scheme:

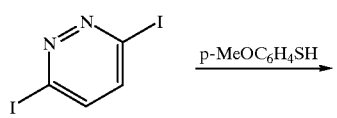

-continued

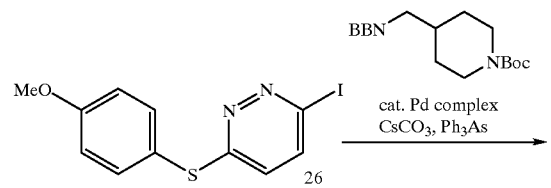

-continued

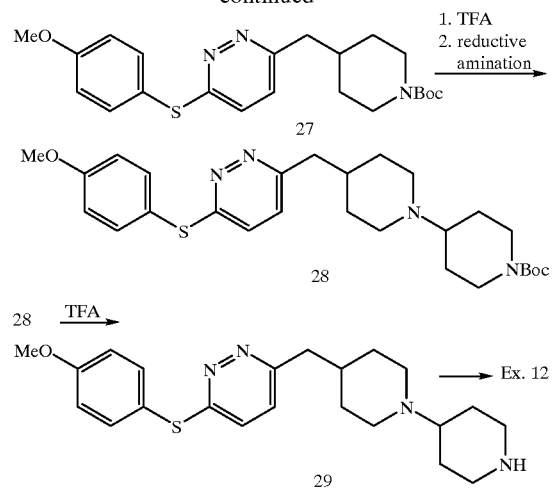

Step 1: Stir diiodopyridazine (3.4 g) and p-methoxybenzenethiol (1.4 g) in CH$_2$Cl$_2$ (40 mL) and add diazabicycloundecane (DBU; 2 mL) dropwise. Stir for 1.5 h., dilute with hexanes (50 mL) and chromatograph on silica gel, eluting with a gradient of CH$_2$Cl$_2$ in hexanes. Evaporate the product fractions and recrystallize from ether-hexanes to give pure 26 (1.65 g), mp 113–114° C.

Step 2: Stir 1-(t-butoxycarbonyl)-4-methylenepiperidine (0.86 g) in 0.5M 9-BBN/THF (9 mL) ar RT for 1 h. under N₂. Add 26 (1.33 g), DMF (9 mL), water (1 mL), triphenylarsine (0.10 g), Pd(dppf)Cl₂ complex (0.10 g) and Cs₂CO₃ (2.0 g) and heat at 90° C. for 2.5 h. Extract in water-CH₂Cl₂, dry over MgSO₄ and evaporate, then pump to remove DMF. Chromato-graph on silica gel, eluting with a gradient of ether in CH₂Cl₂. Combine and evaporate pure product fractions to give 27 (1.13 g), mp 90–92° C.

Step 3: Stir compound 27 (0.5 g) in TFA (4 mL), water (0.25 mL) and CH₂Cl₂ (2 mL) at RT for 1 h., evaporate, add 1 N NaOH and extract with several portions of CH₂Cl₂. Dry over MgSO₄, evaporate and to the residue add CH₂Cl₂ (6 mL), 1-Boc-4-piperidinone (0.33 g) NaBH(OAc)₃ (0.4 g). Stir 24 h., wash with 1N NaOH, dry, evaporate and chromatograph on silica gel with a gradient of CH₃OH in CH₂Cl₂. Evaporate the pure fractions to give 28 as a foam (0.44 g).

Step 4: Stir 28 in TFA (4 mL) for 2 h., evaporate and workup in 1N NaOH with CH₂Cl₂ extractions. Dry and evaporate to obtain the product 29 as a pale yellow solid (0.33 g). HRMS found: 399.2220; theory for MH+= 399.2219.

Step 5: Stir 29 (0.04 g) in CH₂Cl₂ (3 mL) with 1 N NaOH (3 mL) and 6-chloronaphthoyl chloride (0.05 g) for 0.5 h. Separate the organic phase, add CH₃OH (20 mL) and evaporate. Isolate the product by preparative t.l.c., eluting with EtOAc, and convert to the HCl salt as described Example 8. The title compound (0.025 g) was obtained as a pale yellow powder, mp 180–190° C. with decomposition.

Example 13

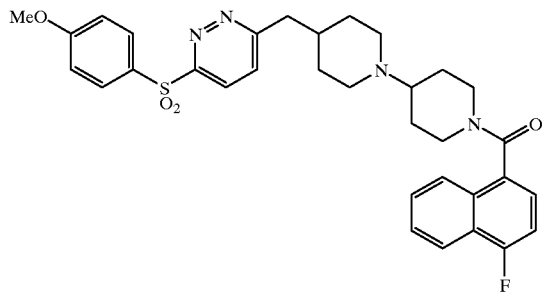

Reaction scheme:

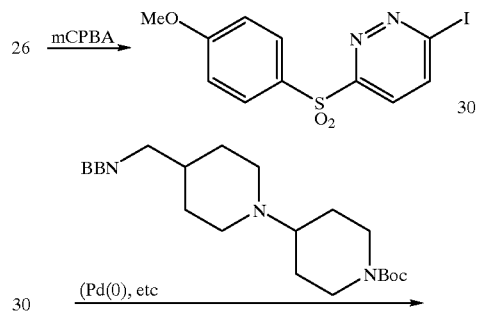

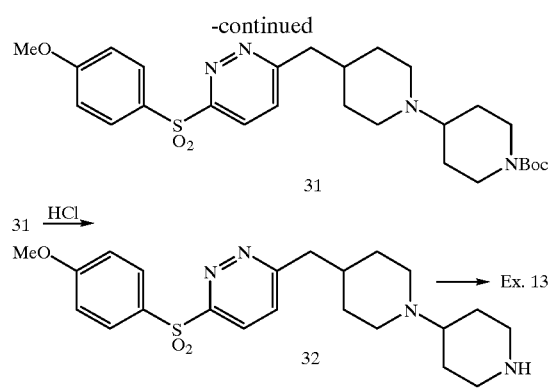

Step 1: Stir the sulfide 26 (0.24 g) in CH₂Cl₂ (5 mL) and add mCPBA (85%; 0.4 g). Stir at RT for 3 h., dilute with CH₂Cl₂ and wash with aqueous solutions of Na₂SO₃ and then NaHCO₃. Dry, evaporate and recrystallize from CH₂Cl₂-hexanes to give the product 30 as white crystals (0.23 g), mp 193–196° C.

Step 2: Heat a solution of 1-(tert-butoxycarbonyl)-4-[(4-methylene)-piperdin-1-yl]-piperidine (0.20 g) in 0.5M 9-BBN-THF (1.6 mL) under nitrogen at 60–70° C. for 2 h., then dilute with DMF (2 mL) and water (0.4 mL). Add 30 (0.20 g), triphenylarsine (0.03 g), Pd(dppf)Cl₂ complex (0.022 g) and Cs₂CO₃ (0.36 g), wash in with DMF (1 mL) and heat at 60–70° C. for 1 h. Workup in water with CH₂Cl₂ extractions, wash with water, dry, evaporate and pump at high vacuum and RT for 4 h. Isolate by preparative t.l.c. on silica, eluting with 1:1 hexanes-acetone to obtain 31 as a buff foam (0.16 g). HRMS: Found: 531.2655; MH⁺requires 531.2641.

Step 3: Stir 31 (0.15 g) for 2 h. at RT in EtOAc (3 mL) and conc. HCl 25 (0.7 mL) then dilute with water, discard the EtOAc phase, basify the aqueous phase with excess 2N NaOH and extract with several portions of CH₂Cl₂. Dry over K₂CO₃ and evaporate to obtain the product 32 as a pale brown foam, suitable for subsequent reactions.

Step 4: Stir at RT for 5 h. a mixture of compound 32 (0.035 g), 4-fluoro-naphthoic acid (0.02 g), DMF (1.25 mL), HOBT (0.02 g), diisopropyl-ethylamine (0.05 g) and EDCI (0.04 g). Dilute with aqueous NaHCO₃, extract with CH₂Cl₂, dry over MgSO₄ and evaporate, then pump at high vacuum to remove residual DMF. Isolate the major product by preparative t.l.c. in acetone on silica, and convert the product to the HCl salt as described in earlier preparations, to obtain the title found as a white powder (0.032 g).

Following the procedures of Examples 1 to 13, using the appropriate starting materials and modifications known to those skilled in the art, the additional compounds of the following structure were prepared

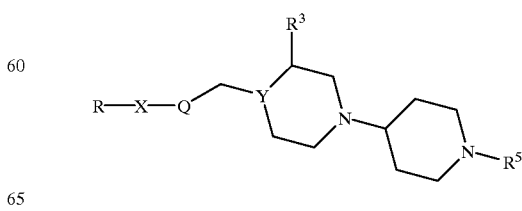

Wherein R, X, Q, Y, R³ and R⁵ are as defined in the table

| Ex. | R | X | Q | Y | R³ | R⁵ |
|---|---|---|---|---|---|---|
| 14 | 4-methoxyphenyl | —SO₂— | 2,5-thienyl | N | CH₃ | propyl-SO₂-CH₂- |
| 15 | 3-methylphenyl | —SO₂— | 2,5-pyridyl | N | CH₃ | 2-methylphenyl-C(O)- |
| 16 | 3-methylphenyl | —SO₂— | 2,5-pyridyl | N | CH₃ | 2-methylphenyl-C(O)- |
| 17 | 3-methylphenyl | —SO₂— | 2,5-pyridyl | N | CH₃ | 1-naphthyl-C(O)- |
| 18 | isopropyl | —S— | 2,5-pyridyl | N | CH₃ | 1-naphthyl-C(O)- |
| 19 | 3-methylphenyl | —SO₂— | 2,5-pyridyl | N | CH₃ | 2-aminophenyl-C(O)- |
| 20 | isopropyl | —S— | 3,6-pyridazinyl | CH | H | 1-naphthyl-C(O)- |
| 21 | 3-methylphenyl | —S— | 2,5-pyridyl | N | CH₃ | 1-naphthyl-C(O)- |
| 22 | 3-methylphenyl | —S— | 2,5-pyridyl | N | CH₃ | 2-methylphenyl-C(O)- |

-continued
| Ex. | R | X | Q | Y | R³ | R⁵ |
|---|---|---|---|---|---|---|
| 23 | 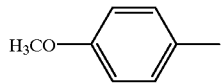 | —SO₂— | 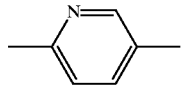 | CH | H | 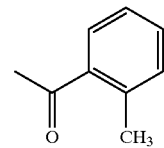 |
| 24 | 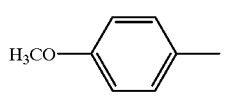 | —SO₂— | 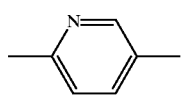 | CH | H | 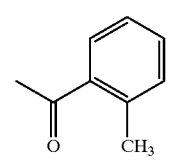 |
| 25 | 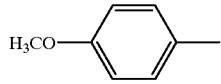 | —SO₂— | 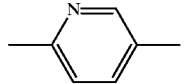 | CH | H | 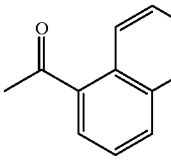 |
| 26 | 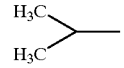 | —S— | 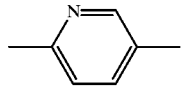 | CH | H | 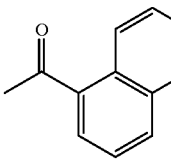 |
| 27 | 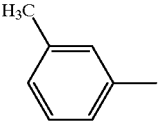 | —SO₂— | 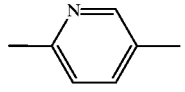 | N | CH₃ | 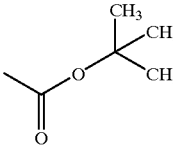 |
| 28 | 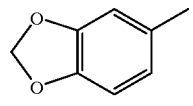 | —SO₂— | 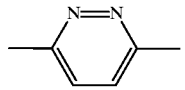 | N | H | 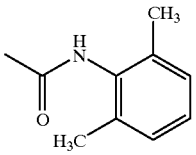 |
| 29 | 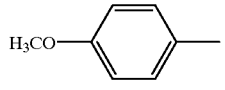 | —SO₂— | 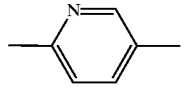 | CH | H | 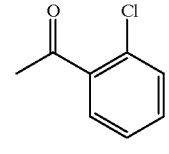 |
| 30 | 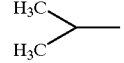 | —S— | 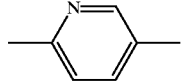 | N | H | 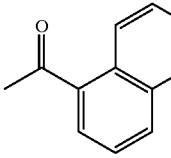 |
| 31 | 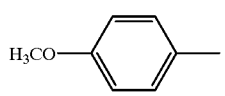 | —SO₂— | 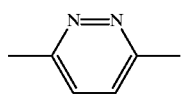 | CH | H | 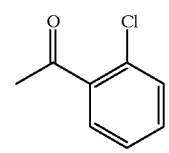 |

-continued
| Ex. | R | X | Q | Y | R³ | R⁵ |
|---|---|---|---|---|---|---|
| 32 | 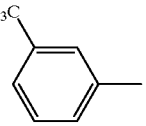 | —SO₂— |  | N |  CH₃ | H |
| 33 | 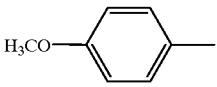 | —SO₂— |  | CH | H | H |
| 34 | 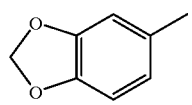 | —SO₂— | 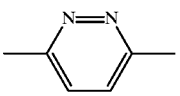 | N | H | 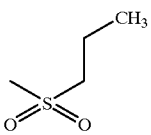 |
| 35 | 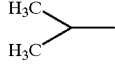 | —O— |  | CH | H | 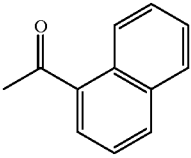 |
| 36 | 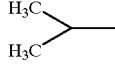 | —S— |  | N | H | 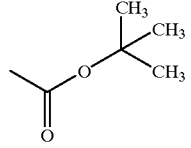 |
| 37 | 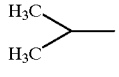 | —S— | 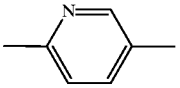 | CH | H | 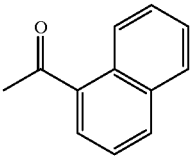 |
| 38 | 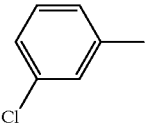 | —SO₂— | 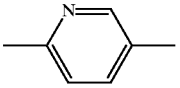 | CH | H | 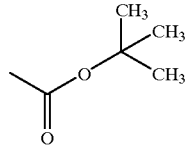 |
| 39 | 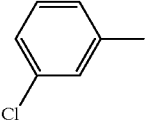 | —SO₂— | 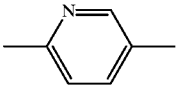 | CH | H | H |
| 40 | 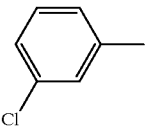 | —SO₂— | 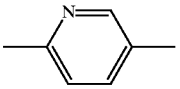 | CH | H | 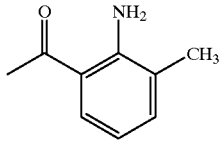 |

-continued

| Ex. | R | X | Q | Y | R³ | R⁵ |
|---|---|---|---|---|---|---|
| 41 | 3-chlorophenyl | —SO₂— | 2,5-pyridyl | CH | H | 1-(2-amino-3-chlorophenyl)ethanone-yl |
| 42 | 3-chlorophenyl | —SO₂— | 2,5-pyridyl | CH | H | 1-(2-amino-3-fluorophenyl)ethanone-yl |
| 43 | 3-chlorophenyl | —SO₂— | 2,5-pyridyl | CH | H | 1-(2-amino-3-methoxyphenyl)ethanone-yl |
| 44 | 3-chlorophenyl | —SO₂— | 2,5-pyridyl | CH | H | 1-(2-amino-4-fluorophenyl)ethanone-yl |
| 45 | 3-chlorophenyl | —SO₂— | 2,5-pyridyl | CH | H | 1-(2-amino-5-fluorophenyl)ethanone-yl |
| 46 | 3-chlorophenyl | —SO₂— | 2,5-pyridyl | CH | H | 1-(2-aminophenyl)ethanone-yl |
| 47 | 4-methoxyphenyl | —SO₂— | 2,5-pyridyl | CH | H | tert-butoxycarbonylmethyl |
| 48 | 4-methoxyphenyl | —SO₂— | 2,5-pyridyl | CH | H | H |
| 49 | 4-methoxyphenyl | —SO₂— | 2,5-pyridyl | CH | H | 1-(2-amino-3-fluorophenyl)ethanone-yl |

| Ex. | R | X | Q | Y | R³ | R⁵ |
|---|---|---|---|---|---|---|
| 50 | H₃CO-C₆H₄- | —SO₂— | pyridine (2,5-) | CH | H | 2-amino-3-chloro-phenyl ketone |
| 51 | H₃CO-C₆H₄- | —SO₂— | pyridine (2,5-) | CH | H | 2-amino-phenyl ketone |
| 52 | 3-Cl-C₆H₄- | —SO₂— | pyridine (2,5-) | CH | H | 2-amino-3-fluoro-phenyl ketone |
| 53 | H₃CO-C₆H₄- | —SO₂— | pyridine (2,5-) | CH | H | 2-amino-3-methyl-phenyl ketone |

Physical data for compounds 14–52 are shown in the table below:

| Ex. | Physical Data |
|---|---|
| 14 | mp = 195–197° C. (decomposition) |
| 15 | mp = 144–147° C. (decomposition) |
| 16 | mp = 147–151° C. (decomposition) |
| 17 | mp = 143–149° C. (decomposition) |
| 18 | mp = above 136° C. (decomposition) |
| 19 | mp = 134–137° C. (decomposition) |
| 20 | HRMS found: 587.2250 |
| 21 | HRMS found: 551.2851 |
| 22 | HRMS found: 515.2848 |
| 23 | HRMS found: 548.2575 |
| 24 | HRMS found: 612.1517 |
| 25 | HRMS found: 584.2596 |
| 26 | HRMS found: 488.2739 |
| 27 | HRMS found: 529.2840 |
| 28 | HRMS found: 593.2546 |
| 29 | mp = 144–149° C. (decomposition) |
| 30 | mp = above 175° C. (decomposition) |
| 31 | HRMS found: 537.2097 |
| 32 | HRMS found: 429.2330 |
| 33 | HRMS found: 399.2220 |
| 34 | HRMS found: 552.1951 |
| 35 | HRMS found: 473.2910 |
| 36 | mp = above 250° C. (decomposition) |
| 37 | mp = above 181° C. (decomposition) |
| 38 | mp = 129–134° C. |
| 39 | mp = above 182° C. (decomposition) |
| 40 | mp = above 161° C. (decomposition) |
| 41 | mp = above 109° C. (decomposition) |
| 42 | mp = above 133° C. (decomposition) |
| 43 | mp = above 139° C. (decomposition) |
| 44 | mp = above 153° C. (decomposition) |
| 45 | mp = above 155° C. (decomposition) |
| 46 | mp = above 161° C. (decomposition) |
| 47 | HRMS found: 530.2664 |
| 48 | HRMS found: 430.2171 |
| 49 | HRMS found: 567.2455 |
| 50 | HRMS found: 583.2154 |
| 51 | mp = above 165° C. (decomposition) |
| 52 | HRMS found: 571.1939 |
| 53 | HRMS found: 563.2712 |

Example 54

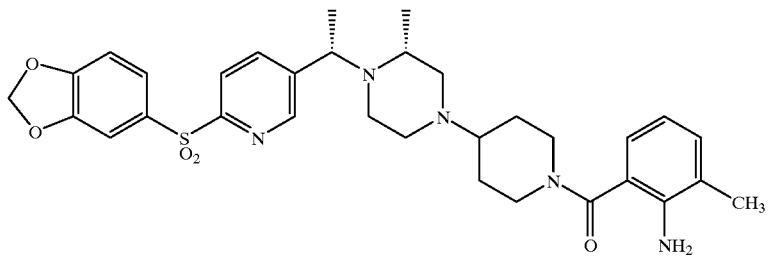

Step 1: A suspension of 6-chloronicotinic acid (5.0 g, 31.85 mmol) in CH$_2$Cl$_2$ (40 mL) containing DMF (0.2 mL) was treated with ClCOCOCl (3.3 mL, 38.22 mmol) and warmed to 40° C. for two h. The resulting clear red solution was cooled to RT and the solvent removed in vacuo. The residue was dissolved in toluene and concentrated again to remove any unreacted ClCOCOCl and traces of HCl. The resulting red gum was dissolved in CH$_2$Cl$_2$ (30 mL). To this solution was added solid N,O—dimethyl hydroxylamine hydrochloride (4.66 g, 47.7 mmol) and iPr$_2$EtN (11 mL, 63.7 mmol). The reaction flask was capped and stirred overnight at RT. After extractive work-up and passage through a short column of silca gel, the Weinreb amide was obtained (5.7 g (yd: 89%)) as an amber syrup. TLC R$_f$=0.5 in 25% EtOAc/CH$_2$Cl$_2$.

Step 2: CH$_3$MgBr (10 mL of a 3M soln.) was added dropwise to a solution of the product of Step 1 (5.7 g, 28 mmol) in 25 mL of dry THF at 0° C., generating a yellow precipitate. After stirring 1 h at RT, the reaction was quenched with saturated NH$_4$Cl solution and the product isolated by extracting with CH$_2$Cl$_2$. The product was purified by flash silica gel chromatography and isolated 3.7 g (84%) as white solid. TLC: R$_f$=0.6 in 25%EtOAc/CH$_2$Cl$_2$.

Step 3: A solution of the product of Step 2 (3.1 g, 20 mmol) and 3,4-methylenedioxyphenyl sulfonic acid sodium salt (4 g, 20 mmol) in dry DMF was heated near reflux for 16 h. The clear yellow solution turned turbid brown and the starting material was completely consumed. The reaction mixture was cooled to RT and quenched with water. Extraction with EtOAc gave 5 g of a dark yellow solid. The product was purified by flash silica gel chromatography and isolated as an off-white solid (3.1g; Yd: 50%). TLC R$_f$=0.4 in 25% acetone-hexane.

Step 4: (S)-2-Methyl oxaborolidine (1M in toluene, 0.5 mL) was added to a solution of the product of Step 3 (0.75 g, 2.46 mmol) in 6 mL of CH$_2$Cl$_2$ and 2 mL of THF at RT. A solution of (CH$_3$)$_2$S.BH$_3$ in THF (2M, 0.74 mL) was introduced dropwise over 4 minutes. After stirring at RT for 1 h, the reaction was quenched with CH$_3$OH and volatiles were removed in vacuo. The residue was dissolved in 20 mL of CH$_2$Cl$_2$ and processed through aqueous extractive work-up to obtain a yellow solid. The product was purified by flash silicagel chromatography to obtain the pure chiral alcohol as a white foamy solid (0.66 g, 88%). TLC: R$_f$=0.3 in 25% acetone-hexane.

Step 5: Et$_3$N (4 mmol, 0.55 mL) and CH$_3$SO2Cl (2.6 mmol; 0.2 mL) were added in sequence to a solution of the product of Step 4 (0.6 g; 1.95 mmol) in 5 mL of CH$_2$Cl$_2$ at 0° C. After stirring and gradual warming to RT over 1.5 h., the reaction mixture was diluted with 10 mL of CH$_2$Cl$_2$ and subjected to an aqueous work-up to remove most of the by-products. Concentration in vacuo gave 0.72 g (96%) of the mesylate as a dark yellow gum. This was redissolved in dry CH$_3$CN (8 mL) and treated with 1-(1-tertbutoxycarbonyl-piperidin-4-yl)-3(R)-methyl-piperazine (0.566 g, 2 mmol) and 2,2,6,6-tetramethyl piperidine (0.33 mL) and refluxed for 8 hours. The reaction mixture was cooled to RT and quenched with water. Extractive work-up in CH$_2$Cl$_2$ provided 1 g of a crude product, which was purified by flash silica gel chromatography using 25% acetone in CH$_2$Cl$_2$ to obtain an intermediate (S,R-diastereomer) as white foamy solid (0.7 g, Yd. =70%) and its R,R-diastereomer (0.1 g, Yd.=10%). TLC: R$_f$=0.55 for S,R-isomer and 0.4 for the R,R-isomer in 25% acetone-CH$_2$Cl$_2$.

Step 6: The product of Step 6 (S,R) was converted to its free base form by treatment with TFA in CH$_2$Cl$_2$ followed by basic extractive work-up to obtain the free piperazino-piperidine as a white foamy solid. To a solution of the free piperazino-piperidine (0.048 g, 0.1 mmol) in CH$_2$Cl$_2$ (1 mL) were added in sequence: EDCI (0.029 g, 0.15 mmol), HOBT (0.020 g, 0.15 mmol), 2-amino-3-methyl-benzoic acid (0.031g; 0.2 mmol) and iPr$_2$Et$_2$N (0.035 mL, 0.2 mmol). After stirring at RT for 10 to 16 h, the reaction mixture was diluted with excess CH$_2$Cl$_2$ and washed with water, 10% citric acid, 10% NaOH solution and brine. The resulting crude product was purified by flash chromatography to obtain the free base form of the title compound as a colorless film (0.055 g, Yd.=91%). Treatment with 1M HCl in Et$_2$O converted it to the HCl salt. mp 180–182° C.

Using a similar procedure and the appropriate acid, the following compounds are prepared:

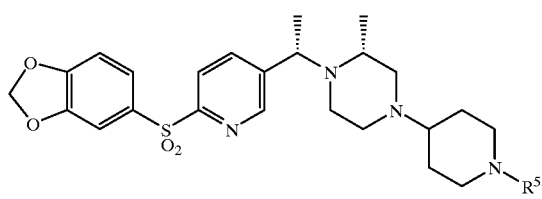

Wherein R⁵ is as defined in the table

| Ex. | R⁵ | Melting Point |
|---|---|---|
| 55 | (1-naphthyl ketone, 5,8-difluoro) | 172–174° C. |
| 56 | (benzoyl, 2-NH₂, 3-Cl) | 184–186° C. |
| 57 | (benzoyl, 2-NH₂) | 187–188° C. |
| 58 | (8-quinolinyl ketone) | 174° C. |
| 59 | (benzoyl, 2,6-dimethyl) | 165° C. |

Examples 60 and 60A

Examples 60 and 60A

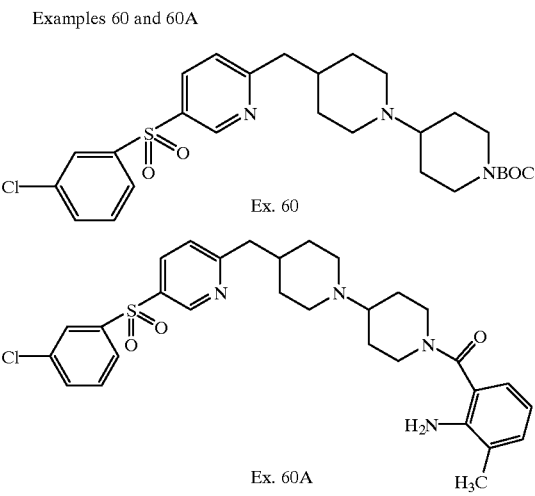

Reaction scheme:

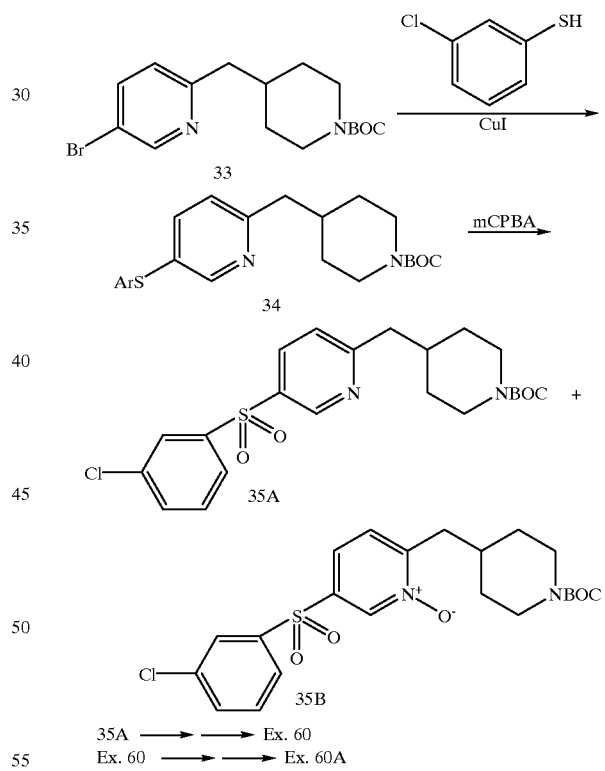

35A ⟶ ⟶ Ex. 60
Ex. 60 ⟶ ⟶ Ex. 60A

Step 1: The procedure of Example 5, step 2, was used for the preparation of 33 using intermediate 11 (7.93 ml), 9-BBN (92 ml), 2,5-dibromopyridine (10 g), DMF (95 ml), H₂O (9.1 ml), K₂CO₃ (7.62 g) and Pd(dppf)Cl₂ (1.03 g). After purification, 33 was isolated as a solid (14.3 g) in 96% yield, mp 66° C.

Step 2: NaH (1.01 g of a 60% dispersion in oil) was washed with hexane (6.0 ml), N,N-dimethyl acetamide (8.4 ml) was added, the resulting mixture was cooled in an ice bath and 3-chlorothiophenol (2.94 ml) was added dropwise. After stirring at RT for 15 min, 33 (3.00 g) and CuI (4.82 g) were added all at once and the resulting mixture was heated at 120° C. for 12 h and then at 140° C. for 4 h. After cooling to RT, EtOAc (150 ml) was added, the mixture was filtered and rinsed with EtOAc. The combined EtOAc portions were washed with water and brine, dried over MgSO$_4$, filtered and evaporated to give a crude oil (4.77 g) which was further purified by column chromatography (silica adsorbent; 225 g; 1:8 EtOAc:hexanes; 1:4 EtOAc:hexanes; 1:2 EtOAc:hexanes as eluant). After evaporation of the appropriate fractions, 34 (1.87 g) was isolated as a waxy solid in 53% yield.

Step 3: 34 (1.00 g) was dissolved in CH$_2$Cl$_2$ (24 ml), the resulting solution was cooled to 0° C., and then mCPBA (1.21 g) was added over 10 min. The resulting mixture was stirred at RT for 24 h. Two new components were noted by TLC analysis (2:1 hexanes:EtOAc). The reaction mixture was diluted with CH$_2$Cl$_2$, made basic (pH=11) with 2 N NaOH and the CH$_2$Cl$_2$ layer was removed. The organic layer was washed with water and brine, dried over MgSO$_4$, filtered and evaporated to give an oil (700 mg) which was further purified by column chromatography (silica adsorbent; 1:8 EtOAc:hexanes; 1:4 EtOAc:hexanes; 1:2 EtOAc:hexanes as eluant). After evaporation of the appropriate fractions, the less polar component, 35A, (196 mg) was isolated as a foam in 18% yield. The more polar component, 35B (339 mg) was isolated as a white foam in 35% yield.

Step 4: The intermediate 35A was treated as in Example 5, steps 3 and 4, to obtain the compound of Example 60.

Step 5: The compound of Example 60 was treated as in Example 5, step 5, followed by the procedure of Example 13, step 4, using 2-amino 3-methyl benzoic acid in place of 4-fluoronaphthoic acid to obtain the compound of Example 60A. After work up and purification, 60A (15 mg) was isolated in its free base form as a foam in 54% yield. HRMS: calc'd: M.H$^+$: C$_{30}$H$_{35}$N$_4$O$_3$SCl: 567.2197; measured: 567.2189.

Example 61 and 61A

Examples 61 and 61A

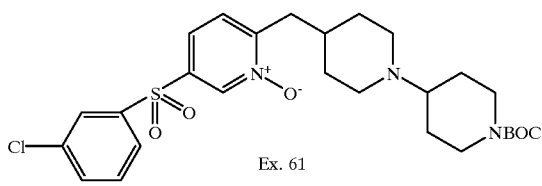

Ex. 61

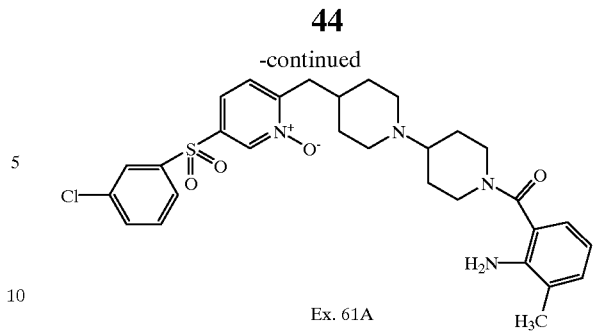

Ex. 61A

Reaction scheme:

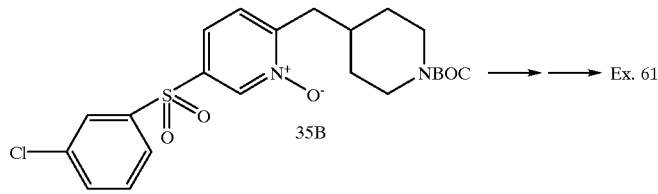

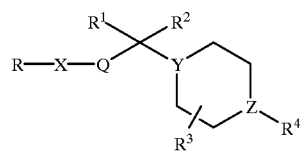

Intermediate 35B was treated in the same manner as 35A to give, initially, the compound of example 61 (48% over 2 steps from 35B) and then example 61A (20% over 3 steps) in hydrochloride form, as a white solid. mp: decompostion above 151°0 C.

What is claimed:

1. A compound having the structural formula

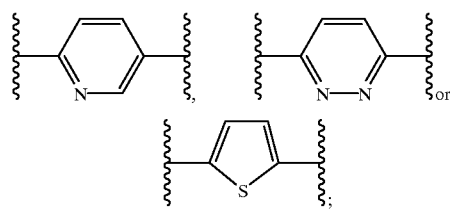

including all stereoisomers and pharmaceutically acceptable salts and solvates thereof, wherein Y and Z are both —N—;

X is —O—, —S—, —SO—, —SO$_2$— or —CH$_2$—;

Q is

[structures shown]

R is (C$_1$–C$_{20}$)alkyl, (C$_3$–C$_{12}$)cycloalkyl, aryl, or R$^8$-aryl;

R$^1$, R$^2$ and R$^3$ are independently selected from the group consisting of H and (C$_1$–C$_{20}$)alkyl;

$R^4$ is $(C_1-C_{20})$alkyl, $(C_3-C_{12})$cyclolalkyl or

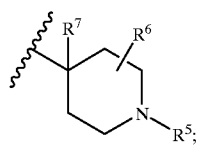

$R^5$ is H, $(C_1-C_{20})$alkyl, $-C(O)(C_1-C_{20})$alkyl, $R^9$-arylcarbonyl, $-SO2(C_1-C_{20})$alkyl, $R^9$-arylsulfonyl $-C(O)O(C_1-C_{20})$alkyl, $R^9$-aryloxycarbonyl, $-C(O)NH-(C_1-C_{20})$alkyl or $R^9$-arylaminocarbonyl;

$R^6$ is H or $(C_1-C20)$alkyl;

$R^7$ is H, $(C_1-C20)$alkyl, hydroxy$(C_1-C_{20})$alkyl or $(C_1-C_{20})$-alkoxy$(C_1-C20)$alkyl;

$R^8$ is 1–3 substituents independently selected from the group consisting of H, $(C_1-C_{20})$alkyl, halogen, hydroxy, $(C_1-C_{20})$alkoxy or hydroxy$(C_1-C_{20})$alkyl, or two adjacent $R^8$ groups may be joined to form a $(C_1-C_2)$alkylenedioxy group; and $R^9$ is 1–3 substituents independently selected from the group consisting of H, $(C_1-C20)$alkyl, halogen, amino or $(C_1-C_{20})$alkylamino.

2. A compound of claim 1 wherein R is 3,4-methylenedioxyphenyl, 3-methylphenyl, 3-chlorophenyl or 4-methoxyphenyl.

3. A compound of claim 1 wherein X is $-CH_2-$ or $-SO_2-$.

4. A compound of claim 1 wherein Q is

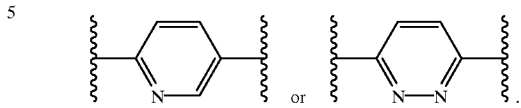

5. A compound of claim 1 wherein $R^1$ and $R^2$ are each H and $R^3$ is H or $CH_3$.

6. A compound of claim 1 wherein $R^4$ is

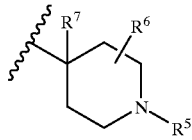

wherein $R^7$ is H or $CH_3$; $R^6$ is H: and $R^5$ is $R^9$-arylcarbonyl.

7. A compound of claim 6 wherein $R^5$ is $R^9$-(1-naphthyl)-C(O)—, o-toluoyl-C(O)— or 2-aminophenyl-C(O)—.

8. A compound as defined in claim 1 selected from the group consisting of

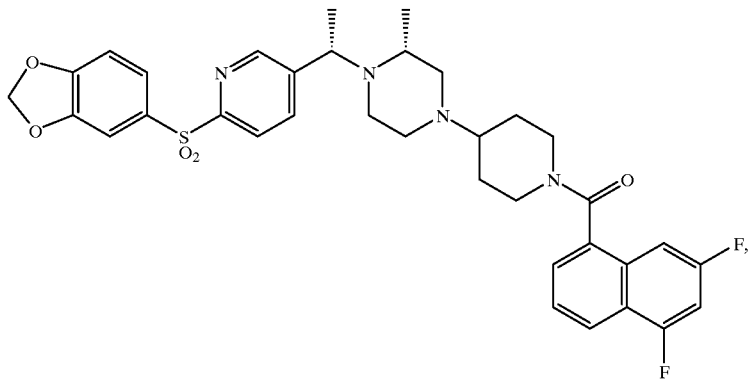

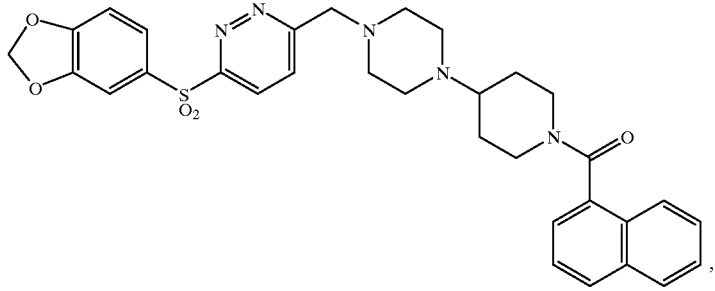

-continued

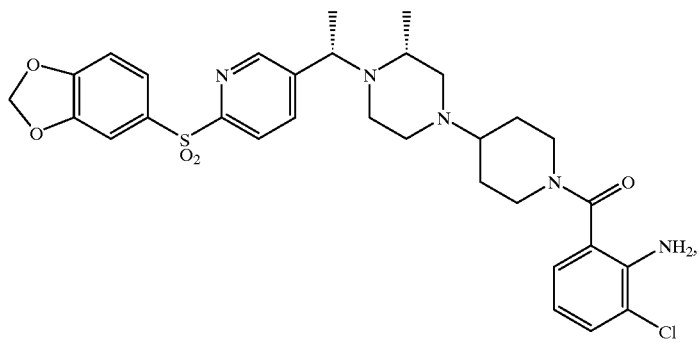

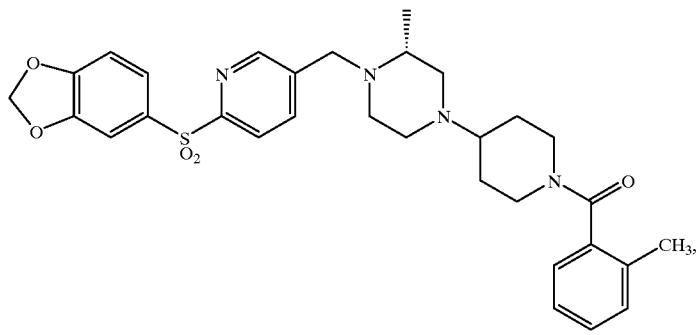

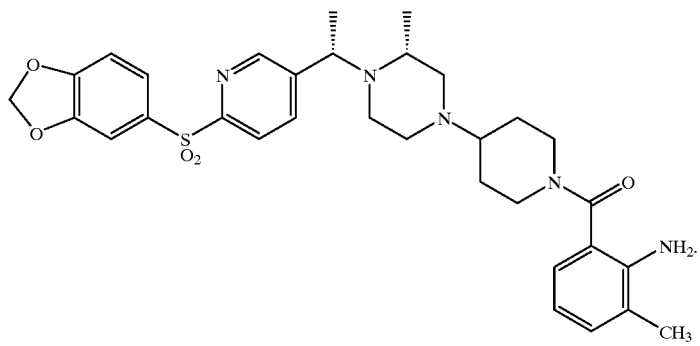

9. A pharmaceutical composition comprising an effective amount of a compound as defined in claim 1 in combination with a pharmaceutically acceptable carrier.

10. A method for improving memory and learning in patients suffering from Alzheimer's disease comprising administering to a patient suffering from said disease an effective amount of a compound of claim 1.

* * * * *